(12) United States Patent
Silverman

(10) Patent No.: US 9,877,681 B2
(45) Date of Patent: Jan. 30, 2018

(54) "MICRO-PATCH" FOR ASSESSMENT OF THE LOCAL MICROVASCULATURE AND MICROCIRCULATORY VASOREACTIVITY

(71) Applicant: David G. Silverman, West Redding, CT (US)

(72) Inventor: David G. Silverman, West Redding, CT (US)

( * ) Notice: Subject to any disclaimer, the term of this patent is extended or adjusted under 35 U.S.C. 154(b) by 0 days.

(21) Appl. No.: 14/626,065

(22) Filed: Feb. 19, 2015

(65) Prior Publication Data

US 2015/0190090 A1    Jul. 9, 2015

Related U.S. Application Data

(63) Continuation-in-part of application No. 12/059,383, filed on Mar. 31, 2008, now Pat. No. 8,961,932, and a continuation-in-part of application No. 14/511,306, filed on Oct. 10, 2014, which is a continuation-in-part of application No. 14/460,082, filed on Aug. 14, 2014, now abandoned.

(60) Provisional application No. 60/920,823, filed on Mar. 30, 2007, provisional application No. 61/865,746, filed on Aug. 14, 2013, provisional application No. 61/889,780, filed on Oct. 11, 2013, provisional application No. 61/927,668, filed on Jan. 15, 2014.

(51) Int. Cl.

| | |
|---|---|
| *A61K 49/00* | (2006.01) |
| *A61B 5/00* | (2006.01) |
| *A61B 5/026* | (2006.01) |
| *A61K 31/04* | (2006.01) |
| *A61K 31/221* | (2006.01) |
| *A61B 5/02* | (2006.01) |
| *A61K 9/00* | (2006.01) |
| *A61K 9/70* | (2006.01) |
| *A61B 5/0285* | (2006.01) |
| *A61B 5/0275* | (2006.01) |
| *A61B 5/145* | (2006.01) |

(52) U.S. Cl.
CPC ........ *A61B 5/4848* (2013.01); *A61B 5/02007* (2013.01); *A61B 5/0261* (2013.01); *A61B 5/6833* (2013.01); *A61K 9/0021* (2013.01); *A61K 9/7038* (2013.01); *A61K 9/7084* (2013.01); *A61K 31/04* (2013.01); *A61K 31/221* (2013.01); *A61B 5/0275* (2013.01); *A61B 5/0285* (2013.01); *A61B 5/14532* (2013.01); *A61B 5/14542* (2013.01); *A61B 5/7257* (2013.01)

(58) Field of Classification Search
USPC ........................................................ 424/9.1
See application file for complete search history.

(56) References Cited

U.S. PATENT DOCUMENTS

| | | |
|---|---|---|
| 5,466,465 A | 11/1995 | Royds et al. |
| 6,417,205 B1 | 7/2002 | Cooke et al. |
| 6,485,431 B1 | 11/2002 | Campbell |
| 6,656,147 B1 | 12/2003 | Gertsek et al. |
| 6,741,895 B1 | 5/2004 | Gafni et al. |
| 2005/0249774 A1 | 11/2005 | Pauletti et al. |
| 2008/0241199 A1 | 10/2008 | Silverman |

OTHER PUBLICATIONS

Kraitl (J. Opt. A: Pure Appl. Opt. 7 (2005) S318-S324).
McGrath (Anesth Analg. Feb. 2011; 112(2): 368-74).
Anderson, T.J., et al., "A Comparative Study of Four Anti-Hypertensive Agents on Endothelial Function in Patients with Coronary Disease", J Am Coll Cardiol 1998, 31:327A, Abst.
Anderson, T.J., et al., "Systemic Nature of Endothelial Dysfunction in Atherosclerosis", Am J Cardiol, 1995, 75:71B.
Anderson, T.J., et al., "The Effect of Cholesterol-Lowering and Antioxidant Therapy on Endothelium-Dependent Coronary Vasomotion". N Engl J Med 1995, 332:488.

(Continued)

*Primary Examiner* — Devang K Thakor
(74) *Attorney, Agent, or Firm* — Welsh Flaxman & Gitler LLC

(57) ABSTRACT

A method is disclosed for assessing local microvasculature and local microcirculatory vasoreactivity of a patient or research subject by selective noninvasive and nondisturbing monitoring of local microvasculature and local microcirculatory vasoreactivity at an accessible site to noninvasive and nondisturbing trans-surface delivery of a study agent with a known microvascular effect in normal subjects. The method includes noninvasively delivering a vasoactive study agent to skin of the subject for trans-surface delivery to the microvasculature. The microvasculature consists of arteriolar-capillary-venule components of an arterial to venous network and the delivery is performed in a non-iontophoretic manner to exclusively affect local microvascular vasoreactivity without systemic effects or changes, wherein the step of delivering includes application of a micro-patch containing the study agent to the skin of the subject. The method also includes determining the subject's microvascular responsiveness by measuring changes in microvascular perfusion in the area of the skin of the subject beneath the micro-patch (including blood flow, blood volume, and/or transfer of blood and tissue components), ensuring that drug delivery does not induce alterations in measurements by delivery to remote sites or by systemic effects and assessing local microvasculature and local microcirculatory vasoreactivity based upon the steps of delivering, determining, and ensuring.

6 Claims, 28 Drawing Sheets

(56) References Cited

OTHER PUBLICATIONS

Bosselier, C., et al., "Impaired Muscarinic Endothelium-Dependent Relaxation and Cyclic Guanosine 5'-Monophosphate . . . ", Journal of Clinical Investigation, 1987, 79:170-4.
Braverman, I.M, et al., "Topographic Mapping of the Cutaneous Microcirculation Using Two Outputs of Laser-Doppler Flowmetry . . . "Microvascular Research, Jul. 1992, 44(1):33-48.
Christen, S, et al., "Dose-Dependent Vasodilatory Effects of Acetylcholine and Local Warming on Skin Microcirculation", Journal of Cardiovascular Pharmacology, 2004, 44:659-64.
Drexler, H., Zeiher, A.M., Progression of Coronary Endothelial Dysfunction in man and its Potential Clinical Significance, Basic Research in Cardiology. 1991, 2:223-32.
Droog, E.J., Sjoberg, F., "Nonspecific Vasodilatation During Transdermal Iontophoresis—the Effect of Voltage Over the Skin", Microvascular Research, 2003, 65:172-8.
Ferrell, W.R., et al., "Elimination of Electrically Induced Iontophoretic Artefacts: Implications for Non-Invasive . . . ", Journal of Vascular Research, 2002, 39:447-55.
Furchgott, R.F., Zawadzki, J.V., "The Obligatory Role of Endothelial Cells in the Relaxation of Arterial Smooth Muscle by Acetylcholine", Nature, 1980, 288: 373-6.
Holowatz, L.A., et al., "Mechanisms of Acetylcholine-Mediated Vasodilatation in Young and Aged Human Skin", Journal of Physiology, 2005, 563:965-73.
Khan, F., et al., "Influence of Vehicle Resistance on Transdermal Iontophoretic Delivery of Acetylcholine and Sodium . . . ", Journal of Applied Physiology, 2004, 97:883-7.
Ledger, P., "Skin Biological Issues in Electrically Enhanced Transdermal Delivery", Advanced Drug Delivery Reviews. 1991, 9:289-307.
Mo, C., Stout, R.G., Shelley, K.H., Tantawy, H., Silverman, D.G., Acute Microcirculatory Effects of Nicotine in Non-Smoking Volunteers, Anesthesiology 2004, 101:A246.
Morris, S.J., Shore, A.C., Tooke, J.E., "Responses of the Skin Microcirculation to Acetylcholine and Sodium Nitroprusside in Patients with NIDDM", Diabetologia, 1337:38-44.
Nissen, A.,et al., "Consistency of Laser Doppler Assessments of Vasoreactivity", American Society of Anesthesiologists, 2006, 2A244.
Nissen, A.F., et al., "Sensitivity of Acetylcholine and Nitroglycerin-Induced Vasodilation to Endothelial Impairment", Anesthesiology, 2007, 107:A291.
Noon, J.P., et al., "Studies with Iontophoretic Administration of Drugs to Human Dermal Vessels in Vivo: Cholinergic . . . ", Br J Clin Pharmacol, 1998, 45:545-50.
Peters, E.J., et al., "The Benefit of Electrical Stimulation to Enhance Perfusion in Persons with Diabetes Mellitus", Journal of Foot & Ankle Surgery, 1998, 37:396-400.
Thanyasiri, P, et al., "Endothelial Dysfunction Occurs in Peripheral Circulation of Patients with . . . ", American Journal of Physiology Heart & Circulatory Physiology, 2005, 289.
Wang, S., Omar, W., Awad, A., Scannell, M., Silverman, D.G., "Direct and Reflexive Autonomic Effects of Acupuncture in Healthy Subjects", Int Anesth Res Soc, 2002, S-215.
Wilkin, J.K., "Poiseuille, Periodicity, and Perfusion: Rhythmic Oscillatory Vasomotion in the Skin", The Journal of Investigative Dermatology, Aug. 1989, 93(2): 113S-118S.
Yoshida, M., et al.,"Impaired Forearm Vasodilatation by Acetylcholine in Patients with Hypertension", Heart & Vessels, 1991, 6:218-23.
"Demise of a Blockbuster Drug Complicates Pfizer's Revamp", Wall Street Journal, Dec. 4, 2006.
Opazo Saez, A.M., et al., "Laser Doppler Imager (LDI) Scanner and Intradermal Injection for InVivo . . . ", British Journal of Clinical Pharmacology, May 2005, 59(5):511-519.
Schonberger, R.B., et al., "Topical Non-Iontophoretic Application of Acetylcholine and Nitroglycerin . . . ", Yale J Biol Med, 2006, 78:229-235.
Silverman, D.G., et al., "Detection and Characterization of Cholinergic Oscillatory Control in the Forehead Microvasculature . . . ", Microvasc Res, 2001, 61:144-7.
Silverman, D.G., et al., "Distinction Between Aropine-Sensitive Control of Microvascular and Cardiac Oscillatory Activity", Microvasc Res, 2002, 63:196-208.
Wardell, K., et al., "Spatial Heterogeneity in Normal Skin Perfusion Recorded with Laser Doppler Imaging and Flowmetry", Microvascular Research, Jul. 1994, 48(1):26-38.
Anderson, T.J., et al., "Close Relation of Endothelial Function in the Human Coronary and Peripheral Circulations", JACC, 1995, 26(5): 1235-1241.
Bjarnason and Fischer. Contact Dermatitis. Sep. 1998;39(3):112-8.
Scheindlin. Molecular Interventions. Dec. 2004;4(6):308-312.
Saez et al. Br J Clin Pharmacol. 2005 59(5):511-19.
Suzuki (Stroke. 1993;24:1049-1053).
Kaski (Circulation 74, No. 6, 1255-1265, 1986).
Benjamin (Hypertension. 1995; 25: 918-923).

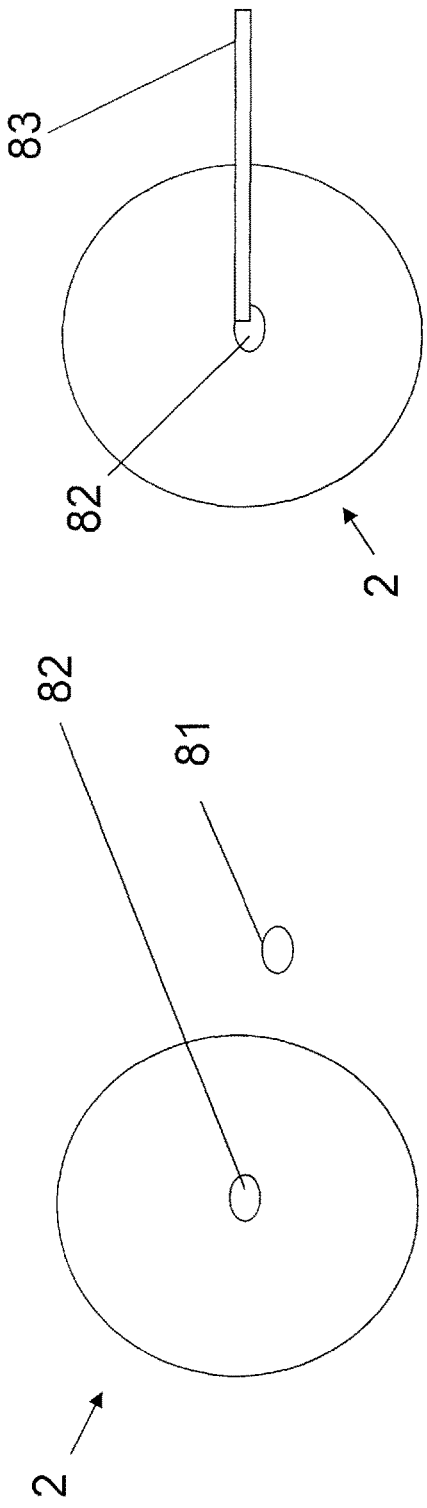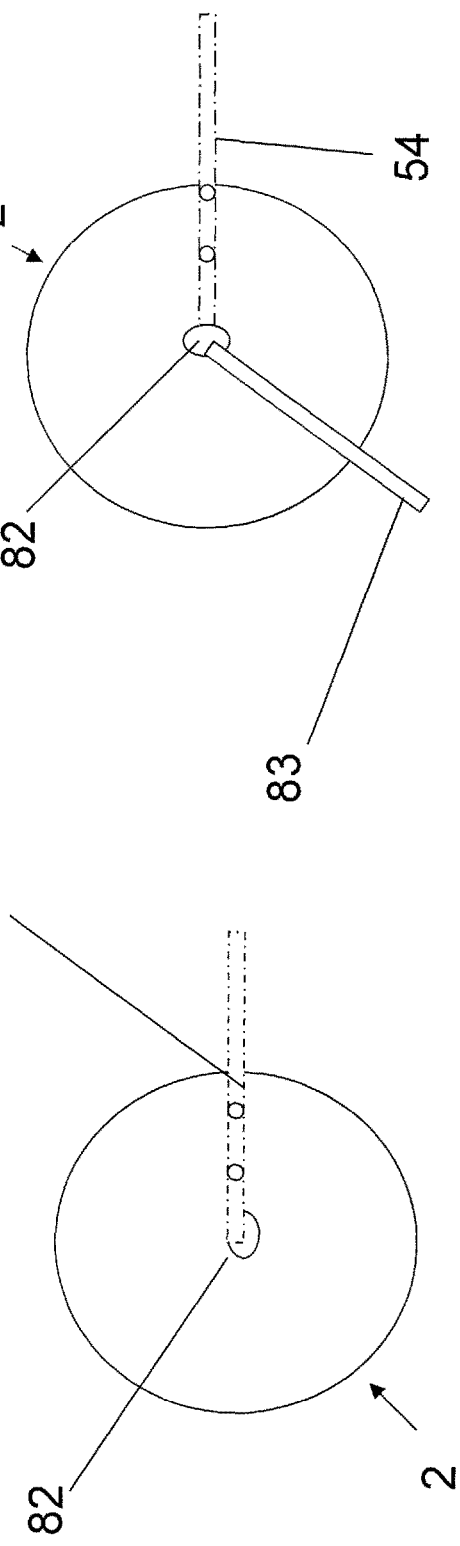

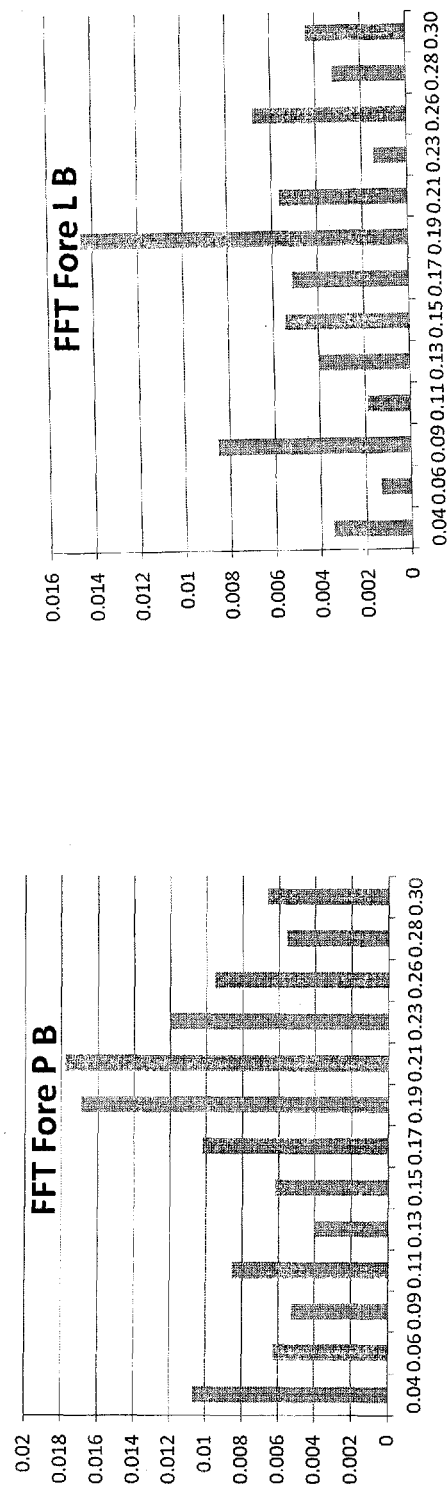
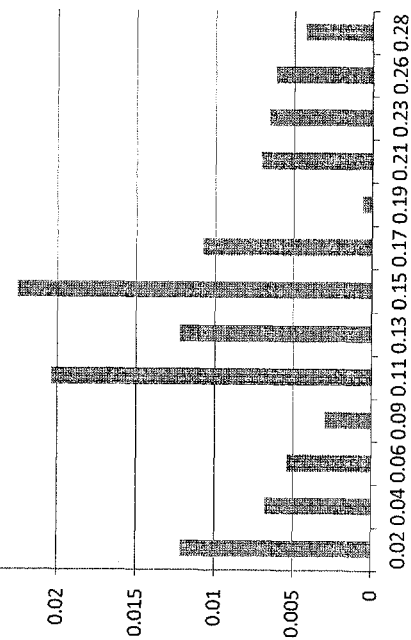
Fig. 25

"MICRO-PATCH" FOR ASSESSMENT OF THE LOCAL MICROVASCULATURE AND MICROCIRCULATORY VASOREACTIVITY

CROSS REFERENCE TO RELATED APPLICATION

This application is a continuation-in-part of U.S. patent application Ser. No. 12/059,383, entitled "'MICRO-PATCH' FOR ASSESSMENT OF THE LOCAL MICROVASCULATURE AND MICROCIRCULATORY VASOREACTIVITY," filed Mar. 31, 2008, which claims the benefit of U.S. Provisional Patent Application Ser. No. 60/920,823, filed Mar. 30, 2007, entitled "'MICRO-PATCH' FOR ASSESSMENT OF THE LOCAL MICROVASCULATURE AND MICROCIRCULATORY VASOREACTIVITY," and this application is a continuation-in-part of U.S. patent application Ser. No. 14/511,306, entitled "METHOD AND SYSTEM ENABLING PHOTOPLETHYSMOGRAPH MEASUREMENT OF VOLUME STATUS," filed Oct. 10, 2014, which is currently pending, which is a continuation-in-part of U.S. patent application Ser. No. 14/460,082, filed Aug. 14, 2014, entitled "METHOD AND SYSTEM ENABLING PHOTOPLETHYSMOGRAPH MEASUREMENT OF VOLUME STATUS," which is currently pending, which claims the benefit of U.S. Provisional Application Ser. No. 61/865,746, filed Aug. 14, 2013, entitled "CONVERTING PHOTOPLETHYSMOGRAPHIC VOLTAGE TO A VOLUME MEASUREMENT: UNIQUE APPLICATION OF THE AC COMPONENT TO NORMALIZE FOR SIGNAL ATTENUATION WITHIN AND AMONG SUBJECTS," U.S. Provisional Application Ser. No. 61/889,780, filed Oct. 11, 2013, entitled "CONVERTING PHOTOPLETHYSMOGRAPHIC (PPG) VOLTAGE TO A VOLUME MEASUREMENT: UNIQUE APPLICATION OF THE AC COMPONENT TO NORMALIZE FOR SIGNAL ATTENUATION, ESTABLISH A VOLTAGE TO VOLUME CONVERSION FACTOR AND ELIMINATE IMPACT OF BACKGROUND," and U.S. Provisional Application Ser. No. 61/927,668, filed Jan. 15, 2014, entitled CONVERTING PHOTOPLETHYSMOGRAPHIC (PPG) VOLTAGE TO A VOLUME SIGNAL: ADDITIONAL MODIFICATIONS TO IMPROVE UTILITY IN CLINICAL AND INVESTIGATIVE SETTINGS, all of which are incorporated herein by reference.

BACKGROUND OF THE INVENTION

1. Field of the Invention

The invention relates to a system(s), method(s) and apparatus(es) for assessment of local microvasculature and microcirculatory vasoreactivity.

2. Description of the Related Art

Multiple studies have indicated that assessment of the microvasculature in an accessible area not only delineates the status of the local microvasculature at that site but also correlates with vascular injury throughout the body, including the heart. [Anderson T J: Assessment and Treatment of Endothelial dysfunction in Humans. J of American College of Cardiology. 1999; 34: 831-838, November 1999; Anderson T J, Uehata A, Gerhard M, Meredith I T, Knab S, Delagrange D, Lieberman E H, Ganz P, Creager M A, Yeung A C, Selwyn A P: Close relation of endothelial function in the human coronary and peripheral circulations. J Am Coll Cardiol 1995; 26(5)1235-1241, Nov 1995; Anderson T J, Meredith I T, Yeung A C, et al.: The effect of cholesterol-lowering and antioxidant therapy on endothelium-dependent coronary vasomotion. N Engl J Med 1995;332:488; Anderson T J, Overhiser R W, Haber H, Charbonneau F: A comparative study of four anti-hypertensive agents on endothelial function in patients with coronary disease. J Am Coll Cardiol 1998;31:327A, Abstract #1147-54] It is particularly relevant to the present invention that Anderson stated: "Endothelial dysfunction, a systemic disturbance of function, precede the presence of atherosclerosis." [Anderson T J: Assessment and Treatment of Endothelial dysfunction in Humans. J of American College of Cardiology. 1999; 34: 831-838, November 1999]. However, the ability to interrogate local microvasculature in a safe, noninvasive, nonintrusive manner has been limited.

In vitro testing of vasoactive drugs typically entails exposure of tissue to different concentrations of an agent (or alternative stimulus) by direct application or by immersion in a drug-containing bath. Such testing led to the discovery in the early 1980's of the importance of the microvasculature and the endothelium lining its vesses; Acetylcholine, a prominent neurotransmitter, causes vasodilation of blood vessels with an intact inner endothelial lining and vasoconstriction of vessels with damaged or missing endothelial lining. [Furchgott R F, Zawadzki J V: The obligatory role of endothelial cells in the relaxation of arterial smooth muscle by acetylcholine. Nature. 1980;288:373-6] While valuable for initial characterization of drug effect, this method is not readily applicable in intact humans and does not necessarily reflect what would happen in an intact preparation; i.e., the findings may not readily transfer to clinical settings. These limitations have prompted in vivo studies in healthy volunteers and patients.

The evaluation in intact humans primarily has been accomplished by systemic administration of a drug (e.g., by a pill, lozenge, solution, or systemic intravenous or intramuscular administration). Systemic administration typically generates direct and indirect responses throughout the body; i.e., at the level of the heart, arteries, arterioles, capillaries, venules and veins. Delineation of effects at the level of the microvasculature is limited by a variety of factors, including:

difficulty obtaining/titrating tissue levels;
difficulty comparing active and placebo effects concurrently;
activation of multiple systemic responses and reflexes which may modulate the effect at the target site;
the potential for unwanted/dangerous systemic effects and side effects, thereby making testing impractical or impossible. For example, the inventor and his colleagues have shown that testing the effects of nicotine on the microvasculature entailed the use of systemic doses (e.g., via lozenges) that resulted in pronounced changes in systemic blood pressure and heart rate that necessitated stopping the study in some subjects. [Mo C, Stout R G, Shelley K H, Tantawy H, Silverman D G: Acute microcirculatory effects of nicotine in non-smoking volunteers. Anesthesiology 2004;101:A246] Likewise, to test the systemic effects of a vasoconstricting drug such as phenylephrine [Silverman D G, Stout R G: Distinction between atropine-sensitive control of microvascular and cardiac oscillatory activity. Microvasc Res 63:196-208, 2002], one may need to deliver doses of drug which can potentially cause significant systemic vasoconstriction and hypertension.

To overcome the aforementioned limitations associated with systemic administration of a drug, investigators have employed selective intravascular injection into a regional artery or vein. Despite the undesirable features of this approach as summarized below, the perceived importance of determining the reactivity of the microvasculature in different disorders has prompted clinicians and investigators to administer pharmacologic agents such as acetylcholine into coronary (heart) as well as brachial (arm) and femoral (leg) arteries. In the context of atherosclerotic disease, intracoronary injection of acetylcholine is associated with impaired vasodilation or frank vasoconstriction, leading to the suggestion that it serve as a test for early detection of coronary artery disease. [Drexler H, Zeiher A M: Progression of coronary endothelial dysfunction in man and its potential clinical significance. *Basic Research in Cardiology.* 1991; 2:223-32; Bossaller C, Habib G B, Yamamoto H, Williams C, Wells S, Henry P D: Impaired muscarinic endothelium-dependent relaxation and cyclic guanosine 5'-monophosphate formation in atherosclerotic human coronary artery and rabbit aorta. *Journal of Clinical Investigation.* 1987;79: 170-4; and Thanyasiri P, Celermajer D S, Adams M R: Endothelial dysfunction occurs in peripheral circulation patients with acute and stable coronary artery disease. *American Journal of Physiology Heart & Circulatory Physiology.* 2005;289]. Likewise, the vasoclilatory response to brachial or femoral artery injection of acetylcholine is compromised in the presence of coronary artery disease [Yoshida M, Imaizumi T, Ando S, Hirooka Y, Harada S, Takeshita A: Impaired forearm vasodilatation by acetylcholine in patients with hypertension. *Heart & Vessels.* 1991; 6:218-23] and hypertension. However, the need for an intra-arterial injection has led to such invasive tests being confined primarily to research settings.

Potential limitations of such regional injection include:
Invasiveness of injection.
Discomfort associated with injection and hence pain-related responses.
Regional pressure and volume changes as a consequence of injections.
The need to apply tourniquets to the regions and/or physically alter blood flow in an alternative manner.
Leakage to the other regions.

Hence, such testing primarily has been confined to research settings.

In an effort to avoid the invasive nature of such injections, investigators have sought other mechanisms for delivery. However, the techniques recommended heretofore have significant shortcomings. Most notably, local injection of drug at the planned site of monitoring can be painful and may produce unreliable results because of local tissue damage and irritation, as well as potential disturbance of tissue planes, thereby leading to inconsistent spread of drug. [Opazo Saez A M, Mosel F, Nurnberger J, Rushentsova U, Gossl M, Mitchell A, Schafers R F, Philipp T, Wenzel R R: Laser Doppler imager (LDI) scanner and intradermal injection for in vivo pharmacology in human skin microcirculation: responses to acetylcholine, endothelin-1 and their repeatability. British Journal of Clinical Pharmacology 59(5):511-519, 2005 May].

This has led to the use of a needleless technique such as iontophoresis, wherein an electrical current drives drug through the skin. As discussed below in greater detail, there are iontophoretic devices that indeed have the ability for drug delivery as well as for laser Doppler monitoring of local blood flow. Such monitoring in the context of iontophoresis has quantified vasodilation at selected sites in response to iontophoretic application of acetylcholine in healthy subjects, and has documented that this response is compromised in patients with diabetes. However, iontophoresis is irritating to the tissue, such that the process itself alters microvascular function and microcirculatory flow; and iontophoretic delivery of vehicle alone causes changes.

While one could wait several minutes after iontophoresis to allow for the effects of electrical current to abate, this also would allow time for the drug to redistribute and potentially leave the local area, especially if the drug has a vasodilatory effect which would increase its uptake by the circulation. Overall, factors limiting the widespread use of iontophoresis in the clinical setting include:

1) it can be painful (this not only would be undesirable for the subject but also might cause pain-induced changes in systemic blood flow);
2) the device requires a well or pad for the drug and is relatively bulky and thus is not necessarily well-suited for placement on small sites such as digits and also on sites that are not perfectly level; moreover, these components may impede monitoring at portions of the delivery/study sites;
3) dosage and time-course are dictated by the need to deliver drug with an electric current;
4) if one has to check periodically to see the effect of iontophoretic delivery on local perfusion while allowing for the direct effect of the electrical stimulation to abate, this could lead to a time-consuming evaluation and undesirable probe repositioning;
5) the vehicle alone (without active drug) can cause changes in local perfusion;
6) iontophoresis can cause an electrical burn under the pad; and
7) electric current itself has been shown to be a potent vasodilator; even when data are modified to account for a potential current-induced effect, the current remains a potential confounder in such studies; its effect varies among specific vehicles and drugs as well as spatially over the area of drug delivery.

The limitations as well as the potential benefits of iontophoresis in the context of disease have been studied extensively. [Christen S, Delachaux A, Dischl B, Golay S, Liaudet L, Feihl F, Waeber B: Dose-dependent vasodilatory effects of acetylcholine and local warming on skin microcirculation. *Journal of Cardiovascular Pharmacology.* 2004;44: 659-64; Noon J P, Walker B R, Hand M F, Webb D J: Studies with iontophoretic administration of drugs to human dermal vessels in vivo: cholinergic vasodilatation is mediated by dilator prostanoids rather than nitric oxide. Br J Clin Pharmacol 1998;45:545-50; Wang S, Omar W, Awad A, Scannell M, Silverman D G: Direct and reflexive autonomic effects of acupuncture in healthy subjects. Int Anesth Res Soc S-215, 2002; Morris S J, Shore A C, Tooke J E: Responses of the skin microcirculation to acetylcholine and sodium nitroprusside in patients with NIDDM. *Diabetologia.* 1337;38: 1337-44; Ledger P: Skin biological issues in electrically enhanced transdermal delivery. *Advanced Drug Delivery Reviews.* 1991;9:289-307; Peters E J, Armstrong D G, Wunderlich R P, Bosma J, Stacpoole-Shea S, Lavery L A: The benefit of electrical stimulation to enhance perfusion in persons with diabetes mellitus. *Journal of Foot & Ankle Surgery.* 1998;37:396-400; Ferrell W R, Ramsay J E, Brooks N, Lockhart J C, Dickson S, McNeece G M, Greer I A, Sattar N: Elimination of electrically induced iontophoretic artefacts: implications for non-invasive assessment of peripheral microvascular function. *Journal of Vascular Research.* 2002;39:447-55; Droog E J, Sjoberg F: Nonspecific vasodilatation during transdermal Iontophoresis—the effect of voltage over the skin. *Micro vascular Research.* 2003;65: 172-8; Khan F, Newton D J, Smyth E C, Belch J J: Influence of vehicle resistance on transdermal iontophoretic delivery of acetylcholine and sodium nitroprusside in humans. *Journal of Applied Physiology.* 2004;97:883-7; Mar and Holowatz L A, Thompson C S, Minson C T, Kenney W L: Mechanisms of acetylcholine-mediated vasodilatation in young and aged human skin. *Journal of Physiology.* 2005; 563:965-73].

Transdermal Drug Delivery:

The known art includes trans dermal applicants (e.g., gels, creams, and ointments that are secured to a supporting substrate or backing)—herein referred to as "patches" because they commonly are supplied in the form of a patch—for a variety of purposes that transdermally deliver drugs in a non-iontophoretic manner (i.e., transdermal (or trans-surface) delivery without the use of electrical energy). However, these patches have limitations due to restricted size and restricted dose. Various patches have been used in the delivery of systemically effective plasma concentrations of a variety of drugs, including:

fentanyl patch for delivery of systemic levels of the analgesic opioid fentanyl, in order to achieve systemic levels commensurate with those by intravenous injection;

scopolamine patch to achieve systemic levels of scopolamine for the treatment of nausea;

nicotine patch to provide systemic levels of nicotine in individuals hoping to wean from cigarettes without symptoms of nicotine withdrawal;

nitroglycerin patch to achieve systemic levels of the cardiac medicine nitroglycerin;

clonidine patch to achieve systemic levels of this antihypertensive medication;

estrogen patch to deliver systemic levels of this hormone; and rivastigmine (Exelon®) patch, an anticholinesterase to inhibit metabolism of acetylcholine in patients with Alzheimer's disease.

As noted above, each of the aforementioned patches is designed to deliver a systemic level of drug and thus, in its current form, is not suitable for the goals of strictly local assessment of the microvasculature. If one of these "systemic patches" were to be used for the purpose of assessing the microvasculature effect of the drug, it would be plagued with most of the limitations and systemic side effects associated with oral or intravenous administration—e.g., remote effects and/or systemic effects.

Prior patch preparations and/or other forms of trans-surface delivery have been designed to achieve a local effect (e.g., to treat local pain, itching, etc.). These include ointments, many of which are in the form of patches:

Lidocaine ointment/patch—delivers lidocaine to a painful site under the patch in the hope of achieving local pain relief.

Tiger Balm® ointment/patch (for local muscle pain).

TheraPatch® (with calamine to treat local itching).

EMLA cream: eutectic mixture of the local anesthetics lidocaine and prilocaine (which is used to provide analgesia in children prior to needle insertion).

Topical phenylephrine has been applied to reduce hemorrhoids. It also has been applied to the vaginal wall to decrease blood flow to distal vaginal sites (beyond the site of application) so as to facilitate assessment of response to sexual stimulation. (see U.S. Pat. No. 6,741,895 to Gafni).

U.S. Pat. No. 6,417,205 to Cooke et al. applied nicotine in a prolonged effort to stimulate angiogenesis—they clearly did not selectively impact the existing local microvasculature; nor were continuous changes in the local microcirculation sought or monitored.

Prior preparations used to achieve a local vascular effect include:

Phenylephrine nose spray to achieve vasoconstriction of nasal mucosa.

Nitroglycerin ointment and 1-arginine ointment to increase local blood flow and thereby improve local healing (based on known vasodilating properties of the drug).

Prior to the present micro-patch for assessment of the microvasculature as disclosed in U.S. patent application Ser. No. 12/059,383, no prior art patch has been introduced or utilized for the diagnosis and assessment of vascular disorders. In addition, except for the local effect of EMLA ("eutectic mixture of local anesthetics"), these prior art patches are designed to cause changes to a relatively large area; 5×5 cm size as opposed to customized limited doses. This can result in significant systemic levels of the drug and thus their use for the assessment of changes in the microvasculature would be compromised. Furthermore, the widespread local delivery will affect much more than the local microvasculature and may encompass multiple vascular beds, including larger arteries and veins. An additional problem of a large delivery area is that it may promote "steal" among vessels in the region as each of the dilated vessels "competes" for increased blood flow.

Monitoring the Local Microvasculature:

As stated above, none of the preparations to date has been designed to include medications for the purpose of measuring microvascular responsiveness; nor have they been adapted for real-time monitoring while the patch is in place. They thus have not been adapted with any mechanism for assessing such flow and have not been accompanied by a placebo patch for the purpose of enabling effective double-blind investigations which isolate the effect of the drug itself as opposed to other variables such as placebo patch application and administration of the vehicle for drug delivery. Additionally, the preparations often are not designed for consistently optimum light transmission, with customization of agent concentration and vehicle color and consistency.

Although multiple mechanisms for assessing surface blood flow have been developed, none of these current mechanisms for assessing surface blood flow is ideally suited for monitoring the changes in perfusion induced by micro-patches in accordance with the present invention and as described below in greater detail. In particular, the shortcomings of the current mechanisms for assessing surface blood flow include:

Thermometry may be more indicative of flow in large vessels than in a restricted microcirculatory bed; the small temperature change that may result from a local microvascular effect induced by a micro-patch is overshadowed by other changes. Furthermore, it is influenced by ambient temperature and the temperature of the patch and its applicant.

Angiography requires radiological contrast material and special detection equipment; moreover, it is relatively ineffective at delineating relatively small changes in the microvasculature.

Capillaroscopy requires a relatively cumbersome microscope and is not suited to monitoring multiple sites.

Radioisotopes entail the use of radioactive material. In accordance with the present invention it has been shown how the delivery and removal of a nonradioactive tracer such as sodium fluorescein may obviate the need for radioactivity (discussed below).

As stated above in the context of iontophoresis, the local microcirculation may be monitored with a light-transmitting technique such as laser Doppler flowmetry. This technique, utilized in preferred embodiments described in the present disclosure, provides noninvasive monitoring of local microvascular flow. The laser Doppler delivers light of uniform wavelength to the tissue under study; this is scattered (phase-shifted) by moving red blood cells near the tissue surface, such that the degree of alteration (recorded in volts as "flux") is proportional to the concentration of moving blood cells and their velocity. As with any of the monitoring techniques that rely upon light transmission, laser Doppler flowmetry would be distorted by surface application of a nontransparent agent or vehicle (which the present invention addresses with transparent/translucent micro-patches). In its simplest form, laser Doppler flowmetry entails placements of a probe on a study site to gain an indication of blood flow. However, a laser Doppler reading is influenced by the number and size of blood vessels under a probe (commonly between 20 and 50 capillaries in one to three arteriolar-capillary networks). Therefore, rather than relying on an absolute value, the technique is primarily used for comparison among sites or to monitor changes at a given site during a challenge (ideally with minimal probe movement). Thus, without the inventive modifications as discussed below in describing the present invention, use of a standard laser Doppler probe with a standard drug patch is prone to error and distortion, most notably: a) most patches have an opaque background, thereby preventing light transmission to the study site; and b) after baseline readings are obtained, the probe would need to be removed to enable patch placement—without special provisions such as those illustrated herein, this leads to distortion as a consequence of spatial heterogeneity (as discussed below). The inventor and his colleagues have documented variability among sites within millimeters of each other. [Braverman I M, Schechner J S, Silverman D G, Keh-Yen A: Topographic mapping of the cutaneous microcirculation using two outputs of laser-Doppler flowmetry: flux and the concentration of moving blood cells. Microvascular Research 44(1):33-48, 1992 July].

The laser Doppler scanning imager scans multiple sites to provide an image of a broader region. However, since it monitors sites sequentially, it does so at the cost of decreased temporal resolution at a given site and hence has the potential for increased temporal artifact (as a consequence of changing conditions as well as subject movement).

The laser speckle imager overcomes the laser Doppler scanner's lack of temporal resolution by acquiring signals simultaneously on a multipixel charged couple device. However, it is not certain as to whether it can generate a successful signal/noise ratio and may not enable optimum sensitivity to gradations in flow; and the speckle pattern is very sensitive to surface irregularities as may result from drug and/or vehicle application; moreover, the degree of speckling may change with time as a cream or ointment is absorbed (even without changes in blood flow).

Plethysmography, most notably photoplethysmography (PPG), offers an alternative means to noninvasively monitor the local microvasculature by monitoring volume under the PPG sensor. Prior to the development of the method and system described herein, it was anticipated that, because it is sensitive to volume in larger vessels, PPG would not be sensitive to changes in the local microvasculature. However, as noted in U.S. patent application Ser. Nos. 12/059,383 and 14/511,306, and discussed below, it may be applied analogous to a laser Doppler so as to monitor micro-patch induced changes in accordance with the objectives of Table 1. Reports of the isolated utilization of PPG to assess the impact of a micro-patch are included herein to demonstrate the utility of the present invention but do not add to the data upon which the application is based. There is an exception—as the present disclosure will herein describe unique hereto undisclosed mechanisms for simultaneous assessments by multiple techniques, including laser Doppler flowmetry+photoplethysmography.

In view of the foregoing, a need exists for improved diagnostic testing systems, methods and apparatuses for integrated use in the assessment of microcirculation. The present invention provides such systems, methods and apparatuses.

SUMMARY OF THE INVENTION

Prior to the development of the current invention, and with the previously discussed shortcomings of prior methodologies as discussed above in mind, assessments of the effects of drugs and alternative agents (herein referred to interchangeably as "drugs", "agents" or "study agents" at the level of the microvasculature (e.g., arterioles, capillaries, venules) were performed primarily in in vitro tissue baths, after systemic drug administration (intravenous, intramuscular, oral), or after driving drug through the skin with electric current. None of these approaches meets the objectives of the present invention as summarized below in Table 1.

TABLE 1

Objectives, Features and Comments Pertaining to Inventive Embodiments Designed to Deliver a Vasoactive Substance[a] to Selectively Impact[b] the Local Microvasculature[c] and Its Component Processes[d] and Monitoring of Resulting Changes in Microvascular Status and Function[e]

| Objective | Features of the Present Invention & Comments |
|---|---|
| 1. To assess status of microvasculature by determining agent[a]-induced changes in microcirculatory function without impacting neighboring or remote sites and/or systemic cardiovascular indices (e.g., heart rate, blood pressure) and/or causing symptoms (e.g, headache, lightheadedness) and/or causing detectable | Integrate features of drug[a] in accordance with dose-responses generated by application to the given site so as to meet objective to selectively impact the local microvasculature (e.g., selectively impact local microvascular perfusion by inducing vasodilation)[b,c]. By limiting impact to local microvasculature without impacting systemic or widespread regional responses, we can utilize local microvasculature as a microcosm representative of the microvasculature in less accessible regions of the body and thus assess the impact of a widespread disorder such as |

TABLE 1-continued

Objectives, Features and Comments Pertaining to Inventive Embodiments Designed to Deliver a Vasoactive Substance[a] to Selectively Impact[b] the Local Microvasculature[c] and Its Component Processes[d] and Monitoring of Resulting Changes in Microvascular Status and Function[e]

| Objective | Features of the Present Invention & Comments |
|---|---|
| blood levels (by concurrent or prior evidence).[bcde] | atherosclerosis on the systemic vasculature (as per documentation of the widespread nature of such disorders in text). Can prepare ingredients for given micro-patch or select readily attainable transdermal preparation (e.g., portion of commercially available available patch) so long as it meets objective to limit site of impact. As a safe starting point for a given agent, each micro-patch in accordance with the present invention has been designed to deliver no more than 10% of that delivered by a "micro-patch" designed to generate systemic levels or that of a drug that has been shown to cause systemic impact when administered by full-sized patch or different route[f]. |
| 2. To determine the vasoactive impact of a drug of uncertain effects being introduced by transdermal administration. | Dosing as per objective #1. Can monitor with multiple parameters within a given device or with multiple devices so as to delineate impacts on acv network[c] and processes associated with a "healthy" network[d]. Can integrate impacts on vasculature (e.g., flow, volume) and blood components (e.g., exogenous tracer, endogenous blood components including a vital substrate such as glucose)[e]. |
| 3. To optimize micro-patch induced increase in blood component delivery and/or removal for clinically measuring a substrate (e.g., blood glucose levels in patients with diabetes) | As per objective #1. However, whereas change of substrate dynamics is used per objective #1 to assess responsiveness of the microvasculature, here (objective #3), the present invention takes advantage of the ability of the inventive micro-patch to improve those dynamics without significant systemic effects and thereby decrease blood ↔ study site interstitium gradients and lag time for assessment of changes in concentration in the blood. |

[a] = micro-patch drug = vasoactive substance = applicant = agent
[b] = selective impact achieved by design that integrates features including: potency of agent, total dose of agent, area of delivery, concentration, rate of delivery and removal, duration of delivery and removal
[c] = microvasculature consists of arteriolar-capillary-venous (acv) components of an arterial (A) to venous (V) AacvV network, a key component of which is the endothelium of the thin-walled capillaries, feeding arterioles and draining venules and local neuronal networks selectively impacting arteriole, capillary and/or venule
[d] = Processes responsible for microvascular dilation and other aspects of microcirculatory control include: release of acetylcholine from intact endothelium; activation of nitric oxide synthetase; release of nitric oxide; activation of guanylate cyclase; release of cyclic GMP; relaxation of vascular smooth muscle, resulting in vasodilation; breakdown of cyclic GMP by phophodiesterase. Conversely, other substances (e.g., norepinephrine) can cause vasoconstriction.
[e] = microvascular function may be assessed by one or more of several monitors specific to the site of micro-patch induced change in perfusion including: change (Δ) in flow (by local laser Doppler flowmetry), Δ volume (by local photoplethysmography), Δ tracer delivery and removal (locally applied fiberoptic fluorometry), and Δ blood constituent delivery wherein constituent may be a substrate that is delivered to the tissue under the probe ("interstitium") such as glucose under a glucose sensor , a gas dissolved in the blood that equilibrates with the site such as carbon dioxide ora product of local metabolism whose removal is dependent on local perfusion.
[f] = Many embodiments entail initially testing, as a default, with a micro-patch that delivers ≤10% of that used clinically to induce a systemic effect and/or with the potential to induce a systemic effect.. However, multiple combinations of doses, concentrations, areas, rates, areas and durations may in accordance with Table 1 objectives, features and/or comments. When multiple agents are employed, initial target of multiple micro-patch embodiments commonly is ≤~15% of total "systemic" dose (i.e., 15% of 100% + 100%) until lack of remote effect is confirmed.

It is, therefore, an object of the present invention to provide a method for assessing local microvasculature and local microcirculatory vasoreactivity of a patient or research subject by selective noninvasive and nondisturbing monitoring of local microvasculature and local microcirculatory vasoreactivity at an accessible site to noninvasive and nondisturbing trans-surface delivery of a study agent with a known microvascular effect in normal subjects. The method includes noninvasively delivering a vasoactive study agent to skin of the subject for trans-surface delivery to the microvasculature. The microvasculature consists of arteriolar-capillary-venule components of an arterial to venous network and the delivery is performed in a non-iontophoretic manner to exclusively affect local microvascular vasoreactivity without systemic effects or changes, wherein the step of delivering includes application of a micro-patch containing the study agent to the skin of the subject. The method also includes determining the subject's microvascular responsiveness by measuring changes in microvascular perfusion in the area of the skin of the subject beneath the micro-patch, ensuring that drug delivery does not induce alterations in measurements by delivery to remote sites or by systemic effects, and assessing local microvasculature and local microcirculatory vasoreactivity based upon the steps of delivering, determining, and ensuring.

It is also an object of the present invention to provide a method wherein the micro-patch has a diameter of approximately 0.25 cm to approximately 2.5 cm.

It is another object of the present invention to provide a method wherein the step of delivering a study agent is regulated to facilitate attainment of baseline readings before delivery of an effective amount of the study agent.

It is a further object of the present invention to provide a method wherein study agents with differing modes of action are administered at the same micro-patch site.

It is also an object of the present invention to provide a method wherein measurements during a plateau phase are obtained within 1-20 minutes after delivery of the study agent.

It is another object of the present invention to provide a method wherein the step of assessing includes assessing magnitude of change in mean, systolic, diastolic and systolic minus diastolic values of individual pulsations, and/or assessing rate of rise or decline of mean, systolic or diastolic values of individual beats, and/or assessing oscillatory patterns among successive beats.

It is a further object of the present invention to provide a method including the step of assessing impact of a transient or persistent condition that may selectively affect a particular component of the microvasculature It is also an object of the present invention to provide a method wherein the microvasculature consists of the endothelium of the thin-walled capillaries, feeding arterioles, draining venules and local neuronal networks.

It is another object of the present invention to provide a method wherein the step of determining is chosen from the group consisting of assessing a change in flow by local laser Doppler flowmetry, assessing a change in volume by local photoplethysmography, assessing a change in local tracer delivery and removal, and assessing a local change in delivery and/or removal of blood and interstitial components.

It is a further object of the present invention to provide a method wherein the step of determining includes assessing a change in local tracer delivery and removal, and a tracer is fluorescein that is monitored by fiberoptic fluorometry.

It is also an object of the present invention to provide a method wherein the step of determining includes assessing a local change in delivery and/or removal of blood and interstitial components, and wherein the component is delivered from blood to local interstitium as for glucose and carbon dioxide and is monitored with a local component-sensitive sensor.

It is another object of the present invention to provide a method wherein a common microvascular receptor that is being assessed in a periphery as an indicator of systemic vasculature is on the microvascular endothelium.

It is a further object of the present invention to provide a method for determining uncertain effects of a study agent on the arterioles, capillaries or venules comprising the microvasculature by selective noninvasive and nondisturbing monitoring of microvascular response to noninvasive and nondisturbing trans-surface delivery of the study agent in an individual in whom a status of the systemic microvasculature already is known. The method includes noninvasively delivering a study agent to skin of a subject for trans-surface delivery to the microvasculature of the subject in a non-iontophoretic manner to exclusively affect local microvascular vasoreactivity without systemic effects or changes, wherein the microvasculature consists of arteriolar-capillary-venule components of an arterial to venous network. The step of delivering includes application of a micro-patch containing the study agent to the skin of the subject. The method also includes determining a microvascular responsiveness of a subject to the study agent by measuring changes in microvascular perfusion in the area of the skin of the subject beneath the micro-patch, ensuring that delivery of the study agent does not induce alterations in measurements by spread to remote sites or by systemic effects, and assessing local microvasculature and local microcirculatory vasoreactivity based upon the steps of delivering, determining, and ensuring.

It is also an object of the present invention to provide a method wherein, for a given study agent, dosing parameters are determined with respect to a rate of delivery and a duration of delivery to provide a desired degree of response in healthy subjects while ensuring lack of confounding effects due to an effect on large vessels.

It is another object of the present invention to provide a method including the step of obtaining a baseline reading prior to delivery of the study agent with a monitor sensitive to microvascular function or microvascular flow.

It is a further object of the present invention to provide a method including the step of monitoring continuously until attainment of plateau phase for up to approximately one hour after onset of effect, wherein monitoring confirms a lack of potentially confounding impact on the study site as a consequence of changes in major vessels, noncontiguous sites, or systemic cardiovascular parameters.

It is also an object of the present invention to provide a system for assessing local microvasculature and local microcirculatory vasoreactivity of a patient or research subject by selective noninvasive and nondisturbing monitoring of local microvasculature and local microcirculatory vasoreactivity at an accessible site to noninvasive and nondisturbing trans-surface delivery of a study agent with a known microvascular effect in normal subjects. The system includes a micro-patch for noninvasive delivery of a study agent to a study surface for trans-surface delivery to the microvasculature of the subject in non-iontophoretic manner to exclusively effect local microvascular vasoreactivity without unwanted system effects, wherein the microvasculature consists of arteriolar-capillary-venule components of an arterial to venous network including neural structures which selectively innervate microvascular components. The system also includes a monitoring probe for monitoring alterations in perfusion of the microvasculature of the subject in only an area of the study surface beneath the micro-patch without alteration of measurements by spread to neighboring sites or deeper vessels or by systemic effects.

It is another object of the present invention to provide a system wherein the micro-patch includes a transparent backing and a protective cover member, and the study agent to be delivered is structured to delay delivery of the study agent.

It is a further object of the present invention to provide a system wherein the micro-patch includes mini-projections.

It is also an object of the present invention to provide a system wherein the micro-patch includes reverse projections that extend into the micro-patch to open up channels for delivery of the study agent.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 10A-10D are a series of schematics of alternate embodiments showing micro-patches provided with an opening in the center of the micro-patch. While typically not necessary in view of the aforementioned embodiments, this provides an alternative for delivery of drug (especially a second drug) and enables monitoring without an intervening patch. FIG. 10A shows the opening. FIG. 10B shows how monitoring can be accomplished via the opening. FIGS. 10C and 10D show how drug delivery may be accomplished not only by simply applying drug via the opening but also viewed microtubules which enable delivery of agent or withdrawal of tracer or substrate to/from the opening as well as to other areas beneath the micro-patch.

FIG. 27 shows three Fast Fourier Transformations (FFT) of the pulse transit times (PTT) at the photoplethysmograph ((PPG) or (P)) and laser Doppler (L) and of the interval PTT between them. Such application of FFT facilitates the comparison of different signals obtained by different monitors (which in this example are on the forehead).

DESCRIPTION OF THE PREFERRED EMBODIMENTS

Figure 1:
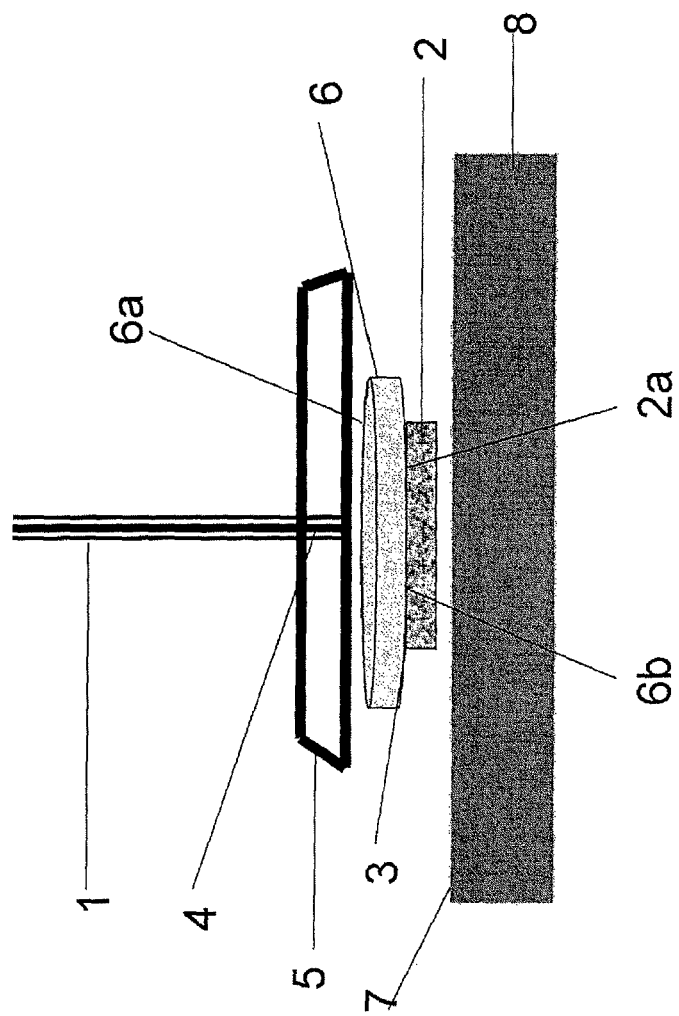
FIG. 1 is a schematic illustrating a preferred embodiment in accordance with the present invention which shows a probe (with its end in a probe holder) atop a double-sided adhesive ring and a micro-patch for adherence to a study site. The figure shows a laser Doppler probe, although an alternative sensor (e.g., photoplethysmographic surface probe or one for quantifying tracer or substrate) could be applied similarly.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

The present invention provides a repeatable, noninvasive, nonintrusive and readily applicable test to interrogate and study the microcirculation of a subject in one or more regions and thereby characterize their function in health and disease, monitor changes in the microcirculation over time, and identify responses in the microcirculation to potentially harmful or beneficial interventions. The present invention introduces apparatuses and methods for: a) focused assessment of the microvasculature that entails noninvasive trans-surface (e.g., transdermal) delivery of a study agent (e.g., a drug with potential microcirculatory effects) and b) a mechanism for noninvasive and repeatable localized monitoring of the microvasculature at the site(s) of agent delivery as well as at untreated sites. The present invention also provides a mechanism for transdermal drug delivery and local assessment of the microcirculation, specifically its ability to respond to the given transdermal agent(s)—e.g., its capacity to vasodilate or its ability to increase the delivery and/or removal of tracer or substrate, wherein compromised tracer and substrate dynamics may reflect decreased microvascular blood flow and/or compromised vascular integrity with restricted transfer across capillary membranes or leakage across such membranes.

This is achieved by interrogating the microcirculation of a subject for use in characterizing function in health and disease, monitoring changes in microcirculation over time, and identifying responses in microcirculation to potentially harmful or beneficial interventions. The method includes delivering a study agent to a study surface for trans-surface delivery to the microvasculature of the subject in a non-iontophoretic manner and monitoring the microvasculature of the subject in the area of the study surface. A system is also provided which includes a micro-patch for delivery of a study agent to a study surface for trans-surface delivery to the microvasculature of the subject in a non-iontophoretic manner and a monitoring probe for monitoring the microvasculature of the subject in the area of the study surface.

The present invention generally relates to a mechanism for local delivery of vasoactive medications and combinations thereof which enables effective monitoring of local vasoreactivity without unwanted systemic effects, a customized modification of monitoring techniques and devices to optimize such testing, and a mechanism for interpreting the findings.

Such interrogation of the local microvasculature has multiple significant clinical implications in that microvascular dysfunction has been observed in patients with a wide variety of disorders including: diabetes (leading to diabetic end-organ disease such as retinopathy, nephropathy, neuropathy, cardiac disease and stroke), atherosclerosis, coronary artery disease, peripheral vascular disease, hypercholesterolemia, hypertension, cigarette smoking, and varied pain states. There is evidence to suggest that dysfunction of microvascular endothelium in an accessible area, such as the skin, correlates with vascular injury throughout the body, including the heart. [Anderson T J: Assessment and Treatment of Endothelial dysfunction in Humans. J of American College of Cardiology. 1999; 34: 831-838, November 1999; Anderson T J, Uehata A, Gerhard M, Meredith I T, Knab S, Delagrange D, Lieberman E H, Ganz P, Creager M A, Yeung A C, Selwyn A P: Close relation of endothelial function in the human coronary and peripheral circulations. J Am Coll Cardiol 1995; 26(5)1235-1241, November 1995; Anderson T J, Meredith I T, Yeung A C, et al.: The effect of cholesterol-lowering and antioxidant therapy on endothelium-dependent coronary vasomotion. N Engl J Med 1995;332:488; Anderson T J, Overhiser R W, Haber H, Charbonneau F: A comparative study of four anti-hypertensive agents on endothelial function in patients with coronary disease. J Am Coll Cardiol 1998;31:327A, Abstract #1147-54]. The availability of a repeatable, noninvasive, nonintrusive and readily applicable test as disclosed in accordance with the present invention facilitates identification of a disorder, documentation of its course, and the effect of therapy. As discussed above in the Background of the Invention section, prior to the present invention a desired mechanism of interrogating the microvasculature in this manner has not been available.

As will be discussed below in greater detail, the present invention employs "micro-patches" (or mini-patches) for selective, local transdermal delivery of vasoactive (and placebo) medications without the need for local injection or application of a driving electric (iontophoretic) current. These contain predetermined and customized consistencies and concentrations of a drug (or biologically active agent) in ointment, gel, cream or liquid or alternative vehicle for application in customized sizes and shapes. While examples of sizes are included herein, in most embodiments, the main limit on the micro-patch is that it be of a size, potency, dose, concentration and vehicle that enables local testing without a systemic effect (See Table 1). Alternatively, the size should not be smaller than the sensing area of the monitoring probe. Micro-patches that are larger than desired can be used with a means for blocking drug access to the study site, such as by use of an impenetrable disk (for example, a double-sided adhesive ring 6 as discussed herein) beneath the micro-patch that only allows exposure of 59.4-mm$^2$ of the micro-patch.

To enable effective transmission of light signals for light transmission monitoring techniques, and as will be discussed below in greater detail, the basic inventive "micro-patch" may contain: a) a transparent, translucent or clear backing to enable monitoring through the micro-patch; or b) microfibrils coursing to the monitoring site atop, within and/or below the micro-patch.

Figure 3:
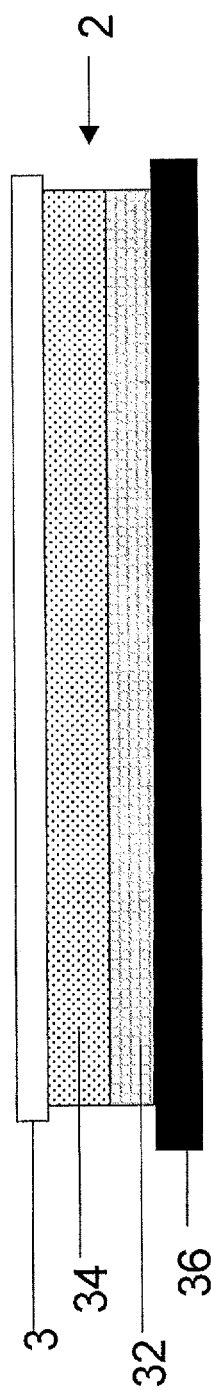
FIG. 3 is a schematic showing a micro-patch in accordance with the present invention with layers showing an inactive layer/matrix that can be customized to delay delivery of drug (or biological agent) and enable baseline readings with the micro-patch in place.
Figure 4:
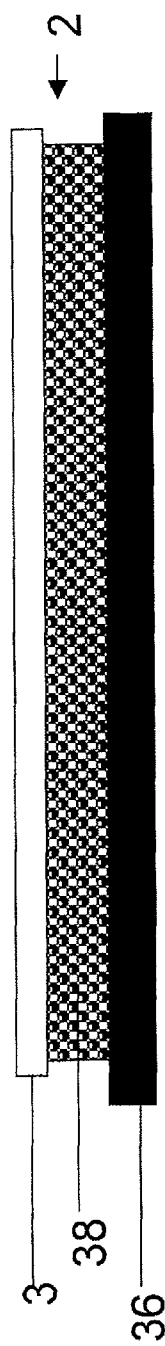
FIG. 4 is a schematic showing a micro-patch in accordance with the present invention with the drug encapsulated to delay its delivery and/or its release after delivery.

Delivery of agent via micro-patch may occur in a variety of ways: a) drug that is active prior to application of monitoring (not preferred because of need for baseline values at the site of drug administration); b) by delayed release from the micro-patch with clear backing as shown with reference to the embodiments in FIGS. 3, 4, 5A and 5B, and as discussed below in greater detail; c) delayed activation of an encapsulated drug such as that shown in FIG. 4 (as by body temperature, chemicals, external ultrasound) after it is delivered; and d) delivery via microfibers that course above, within or below the mini-patch (regardless of backing) as shown with reference to the embodiments in FIGS. 6 and 7 and as discussed below in greater detail.

It is contemplated the micro-patch may have an opening or gap to permit application of another agent and/or to facilitate monitoring while the micro-patch is in place. Although preferred embodiments as described herein set forth the application of the micro-patch to the skin of a subject, it is contemplated application of the micro-patches is not limited to the skin, and may include mucosal surfaces or the surface of another body tissue so long as Table 1 features are customized to the surface under study.

It is further contemplated alternative embodiments may more aptly be referred to as "micro-applicants" that are composed of an aliquot of agent/vehicle without backing. Those applied solely to the skin may be referred to as "micro-derm applicants;" they may be applied with the probe shown in FIG. 15. The site then could be covered by translucent micro-patch backing over the remainder of the probe. For purposes of simplicity, all are referred to herein as "micro-patches."

Figure 25:
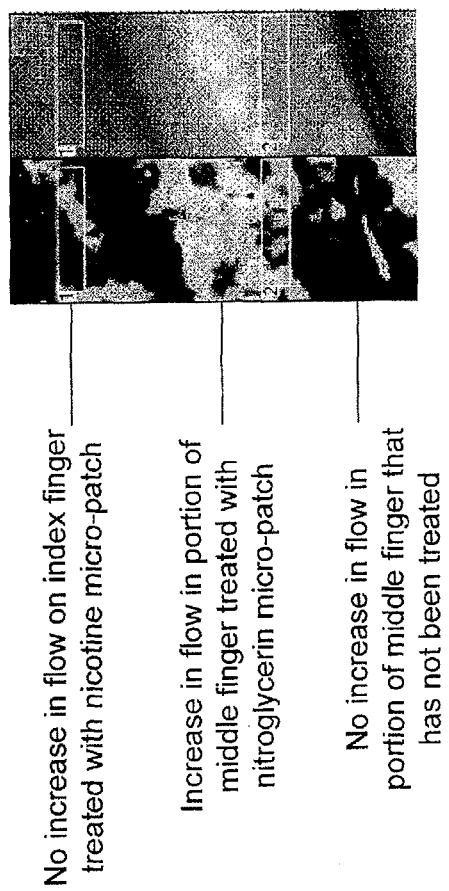
FIG. 25 shows an image and photo obtained with laser Doppler scanner in accordance with the present invention after application of a nicotine micro-patch to index finger and a nitroglycerin micro-patch to middle finger. The fingers have less cholinergic receptors than the forehead. This is supported by the lack of increased flow at the nicotine site. In contrast, flow increased at the nitroglycerin site since the vasodilatory effect of nitroglycerin is independent of said receptors.
Figure 26:
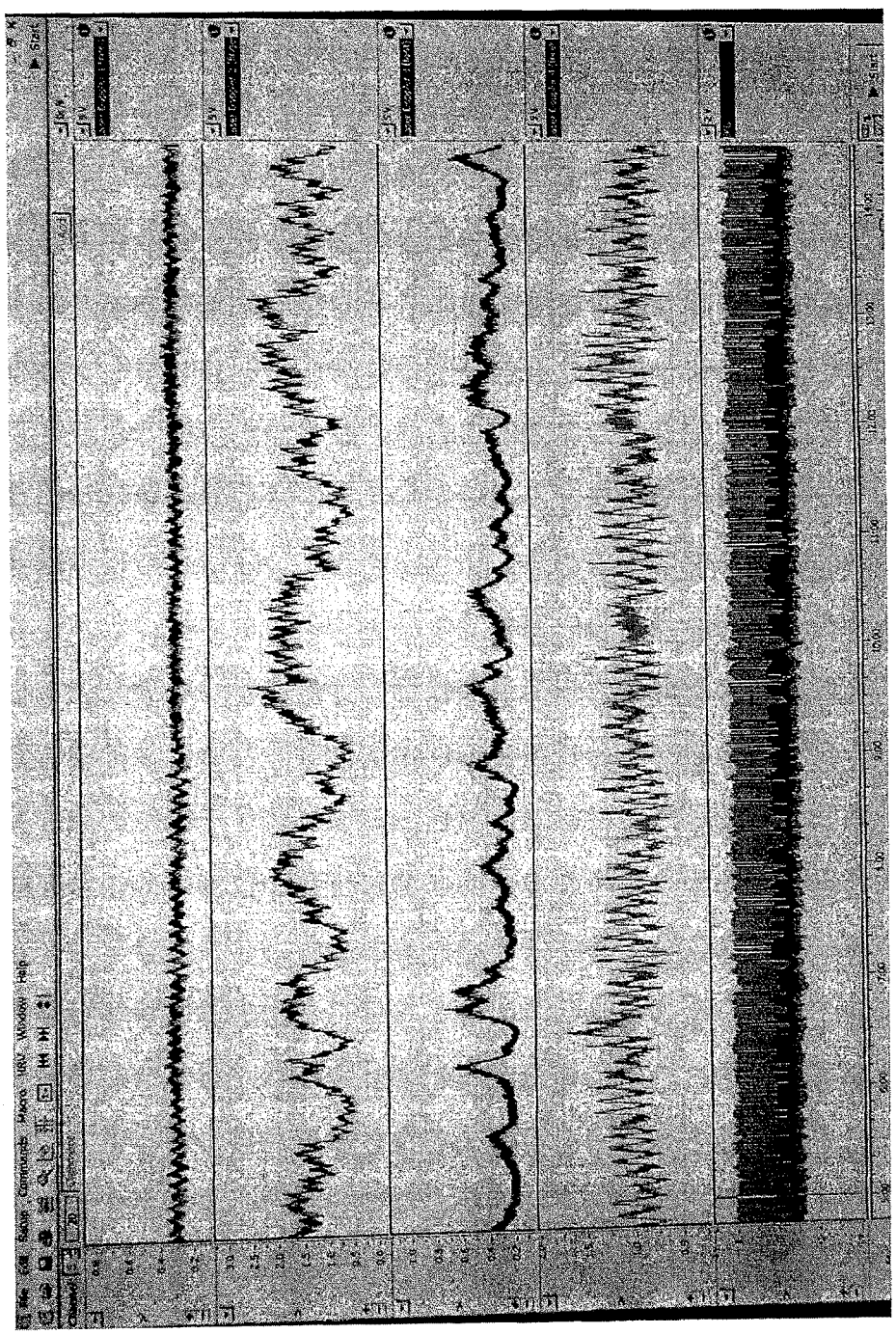
FIG. 26 is a snapshot of a screen showing continuous tracings from multiple channels; time on x-axis, magnitude of each signal on y-axis. It illustrates four laser Doppler signals (from four different sites) and the electrocardiographic tracing so as to monitor changes in heart rate, heart rate variability and even the morphology of the electrocardiogram waveform.

In order to avoid the need to remove monitoring probes for drug application after baseline unless the micro-patch enables delayed release, the application of a micro-patch after baseline is best obtained in embodiments where the monitoring is elevated above the skin as shown in FIGS. 25 and 26.

The inventive micro-patch is designed to constitute one of several different embodiments with the following inventive features:
  sufficient agent and agent delivery to affect the underlying microvasculature, with limited agent delivery so as to prevent unwanted changes at remote sites or undesirable systemic uptake;
  a configuration that enables monitoring of the local microvasculature; e.g., a transparent backing that enables transmission of light signal for laser Doppler flowmetry, laser speckle imaging, and/or photoplethysmography; and
  a configuration that ensures effective delivery throughout the potential areas of the monitoring site.

Figure 12:
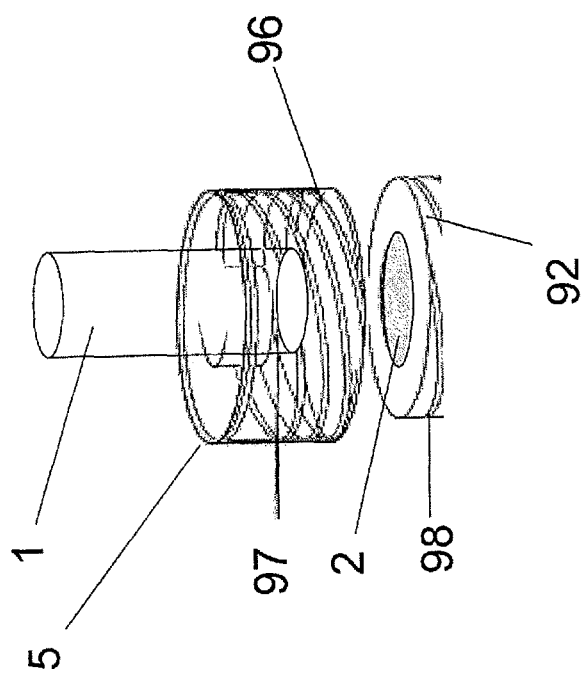
FIG. 12 is a perspective view of a schematic showing a two-component mechanism for engaging and advancing a probe (in this a laser Doppler flowmetry probe). The probe is in a probe holder with threads (or grooves) for threaded engagement with threads on the circumference of a disc encasing the micro-patch. Advancements secure the laser Doppler flowmetry probe and push the micro-patch against the study site.
Figure 13:
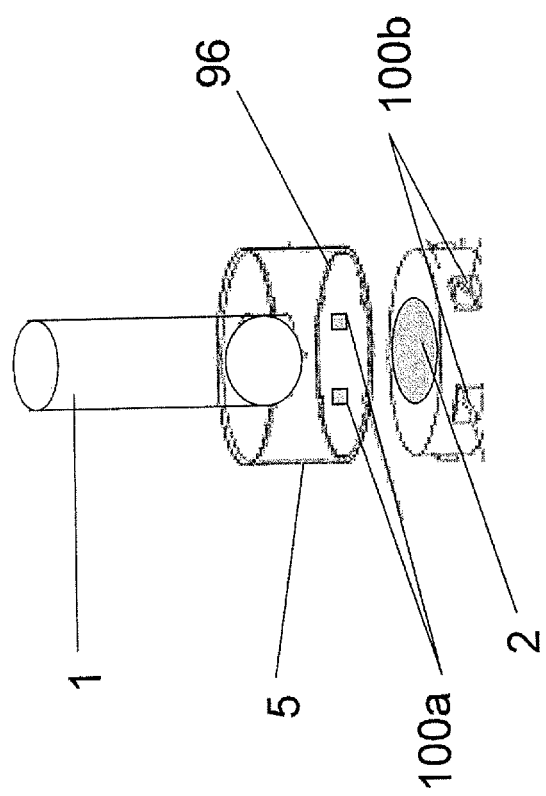
FIG. 13 is a perspective view of a schematic showing an alternative mechanism for advancing and engaging a probe (laser Doppler flowmetry probe) into a probe holder and pushing the micro-patch against the study site. Here, the probe is encased in a probe holder with tabs on the inside of its outer rim. These engage interspaced threads on the circumference of the disc encasing the micro-patch.
Figure 14:
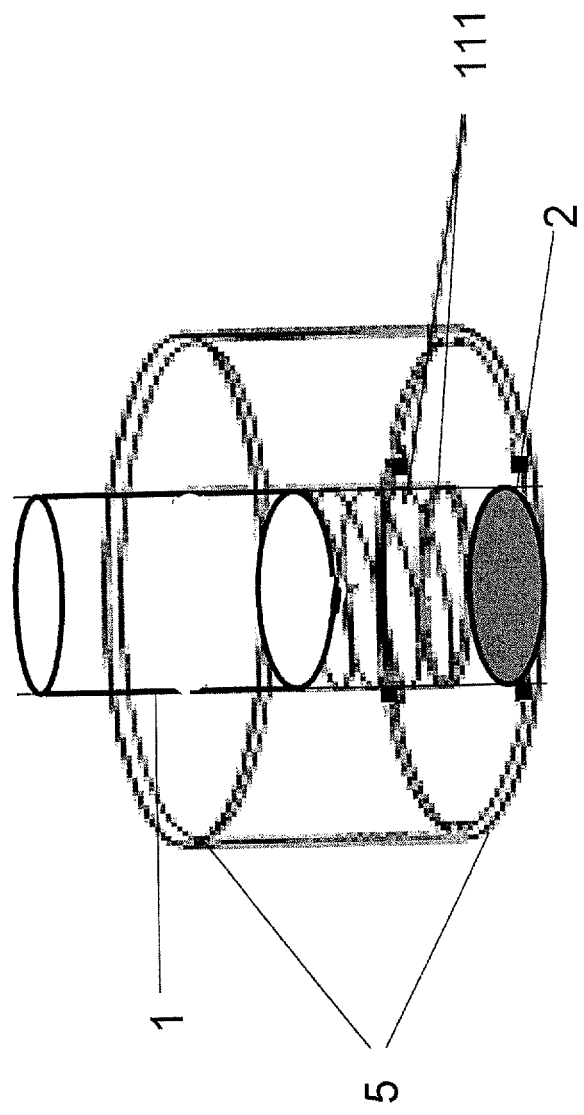
FIG. 14 is a schematic showing a laser Doppler flowmetry probe holder which is separated from the study surface by a spring. After baseline readings are obtained with the micro-patch lying gently on the study surface beneath the spring, the probe and its probe holder are advanced to transiently compress the spring and increase adherence of the micro-patch. Tabs on the probe holder are shaped and dimensioned for threaded engagement with threads on the probe holder (as shown in FIG. 11). Multiple alternatives for comparable engagement and disengagement previously have been described by the inventor (with respect to engaging needles and diaphragms) in U.S. Pat. No. 6,391,014, to Silverman, entitled "STRONG DIAPHRAGM/SAFE NEDDLE/CONVERTING DEVICE COMBINATIONS AND THEIR INDIVIDUAL COMPONENTS", issued May 21, 2002, which is incorporated herein by reference.
Figure 16:
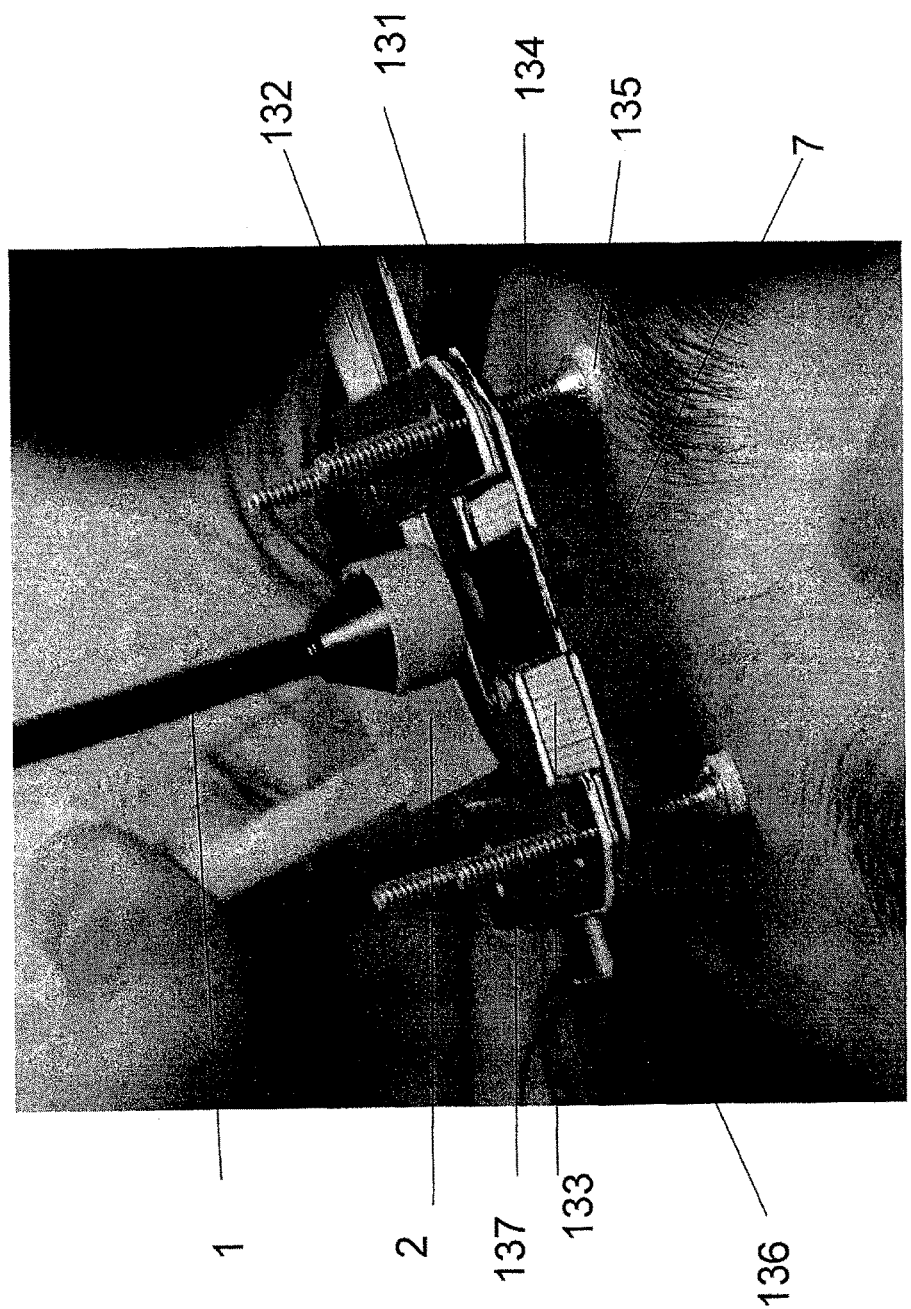
FIG. 16 is a perspective view showing a probe support assembly for mounting a probe (in this case a multichannel probe) above the skin. The support assembly is designed to enable consistent movements in fixed increments (e.g., 1 mm) so as to obtain new measurements without disturbing the alignment of the probe with the skin or an underlying micro-patch. In practice, and as will be discussed below in greater detail, the probe remains undisturbed while a micro-patch is being placed in alignment under the probe.

In accordance with preferred embodiments, the micro-patch may have one of several potential mechanisms to regulate agent delivery so as to:
  enable real-time dose-response assessments; and
  allow for baseline readings prior to inducing a drug response by:
    delaying release of drug from micro-patch already in place—as by encapsulating agent, including an inactive preliminary layer, including a dissolvable membrane;
    delaying adherence of micro-patch to study site until probe is advanced, as shown in FIGS. 12-14; and/or
    delaying delivery of drug to the study site by applying the micro-patch after baseline readings are obtained (as facilitated by a probe that is elevated above the study site as shown in FIG. 16) and/or delaying delivery via embedded tubules or gaps in the micro-patch (as shown in FIGS. 7 and 10A-D). The aim is to enable attainment of baseline data without the need to displace the monitoring equipment to subsequently initiate agent delivery. Additionally, a strip, such as that shown in FIGS. 6 and 7, could be partially peeled back (while remaining anchored in place) so as to allow micro-patch application (if the agent were not already a component of the strip).

An inventive micro-patch may deliver:
a) an agent that previously, has not been available for transdermal administration;
b) an agent that, although previously available for transdermal administration, has not been available as a patch for drug delivery; and/or
c) an agent which is available as a patch for transdermal delivery but which has not heretofore been adapted or utilized for the monitoring of the local microvasculature (or testing its efficacy at the level of the microvasculature).

As of this time, except for those in accordance with the present invention, no patch has been designed for use in the manner described herein in accordance with a preferred embodiment of the present invention.

With respect to "a" above, and in accordance with a preferred embodiment of the present invention, the apparatuses and methods are introduced and described for transdermal ("trans" tissue surface) administration of acetylcholine and phenylephrine; two drugs not previously available for passive transdermal administration (i.e., that previously required injection into a patient's artery or iontophoretic delivery with an electric current as discussed above in the Description of the Related Art section above). It is contemplated the present introduction of transdermal delivery of drug for localized testing of the microvasculature with a given dose of a given agent could readily be adapted to other doses as well as to other agents based upon the teachings provided herein. Specifically, this approach may be applied to any or all of the steps involved in vasoconstriction or vasodilation of the microvasculature, including:

activation or inactivation of receptors;

activation or inhibition of contraction or relaxation of vascular smooth muscle;

production, secretion, removal, or metabolic degradation of vasoactive substances such as nitric oxide, prostacyclin, endothelin, platelet-activating factor; thrombin, bradykinin, ADP and ATP; and/or alteration by inflammatory mediators.

With respect to drugs that already are used for transdermal administration ("b" and "c" above), the present disclosure describes methods, apparatuses, systems, and structures for modifying such agents for the purpose of testing the local microvasculature without remote or systemic changes and undesirable systemic side effects from local drug application.

The micro-patches may be applied for:

testing at small area(s) of seemingly healthy tissue;

testing at multiple areas of healthy tissue with comparable innervation (e.g., relative sympathetic and/or parasympathetic neurovascular control) and perfusion so as to compare responses to the same micro-patches, responses to different micro-patches, and/or to responses to a micro-patch at one site and a different challenge;

testing at multiple areas of healthy tissue with different innervation and/or perfusion to document the vasoreactive properties of the given regions;

testing of multiple agents and/or challenges at a given site; and/or testing at multiple sites with different, unknown or uncertain vessel and tissue integrity (e.g., one site might be injured and/or have compromised healing); comparisons may entail responses to the same micro-patch, different micro-patches, and/or other challenges.

More specific examples include:

Evaluate local vasoactivity and vasoreactivity in diseases such as diabetes, hypertension, and other disorders with a possible vascular component and to characterize the nature of dysfunction based on responses to different agents (e.g., neural, receptor, endothelium-dependent, endothelium-independent) as well as the effects of therapeutic interventions on the responses at said site. An inability to dilate effectively (as may be assessed by monitoring techniques such as laser Doppler flowmetry, photoplethysmography and/or measurement of delivery or removal of tracer or substrate) may signal significant dysfunction with potential tissue injury.

Enable assessment of a topically applied drug in the context of a systemically administered drug or a systemic challenge. This constitutes a unique "dual platform" for assessing the interaction of multiple drugs such as nitroglycerin and sildenafil (Viagra®) wherein one or more drugs could be administered via micro-patch and thereby avoid dangerous systemic levels of two drugs. When used as a component of dual platform, micro-patch can be used to determine:

Whether there is an effect caused by the other challenge; and/or

Whether the effect of the other challenge or intervention is maximal (e.g., effect of nerve block, atherosclerosis, hypovolemia)Whether a known effect of one factor (e.g., exposure to condition which compromises microvascular function or another drug) is reversible by changes consistent with those induced by given micro-patch agent.

Document the potential therapeutic effectiveness of topical application of a drug designed to alter perfusion and potentially improve healing by monitoring effects on local perfusion.

Test microcirculatory vasoactive effects not only of precedented medications (i.e., those with established mechanisms of action) but also of unprecedented medicines.

Determine if a given therapy or intervention has an undesirable effect on the microcirculation:

whether said agent is to be both applied and assessed locally; or whether it is to be administered systemically and assessed locally with respect to its effect on the response of the local microvasculature to the contents of a given micro-patch.

Two prominent, costly examples where testing has not been performed and which may be appropriate for testing in accordance with the present invention are:

The adverse effects of COX2 inhibitors such as rofecoxib (Vioxx, Merck) may have been identifiable by the present invention before its unexpected adverse effects on the microvasculature (causing increased risk of fatal heart injury) became evident during clinical use and caused prompt withdrawal from the market and multiple high-profile law suits; and The adverse effects of torcetrapid (Pfizer) that were not appreciated until relatively late during a 15,000 patient clinical trial (increased cardiovascular morbidity and mortality) may have been identifiable by utilization of the present invention. The drug-induced hypertension may have been due to compromised vasodilatory activity. Use of the present invention also may have identified the vascular abnormality that led to increased signs and symptoms of coronary artery disease. Instead Pfizer was startled by the discovery. According to the Dec. 4, 2006 *Wall Street Journal* ("Demise of a blockbuster drug complicates Pfizer's revamp"), just two days earlier, Pfizer's research chief stated, "We believe this is the most important new development in cardiovascular medicine in years." The sudden and surprising discovery of adverse effects led to a precipitous halt of the study and a double-digit decline in Pfizer stock.

The present invention may be applied to predict whether a given tissue will be able to meet demands for increased perfusion as may be required if the patient is scheduled to undergo surgery at that site (and thus need an increase in blood flow to heal the surgical wound).

As discussed below in greater detail, appropriate drug selection enables delineation of the nature of a vessel abnormality. For example, one can compare the effects of nitroglycerin and acetylcholine:

Nitroglycerin is a nitric oxide donor that causes relaxation of vascular smooth muscle and hence dilation of blood vessels even if the inner endothelial lining of the vessel is damaged; hence it causes endothelium-independent vasodilation.

Acetylcholine is an agent which activates receptors on intact endothelium that then cause local release of nitric oxide; hence it requires an intact endothelium and thereby causes endothelium-dependent vasodilation.

Nicotine induces parasympathetically mediated release of acetylcholine and thereby causes endothelium-dependent vasodilation.

No one has previously disclosed an apparatus, system or method for non-iontophoretic transdermal (trans-surface) delivery of vasoactive agents via translucent micro-patches (or their equivalent) for interrogation of the microvasculature at the site of drug application. While the present invention is considered to represent the first use and adaptation of transdermal micro-patches for the purposes described herein, patches have previously been used in clinical settings. The differences from the prior art include:

the present invention provides for preparations of agents that previously were not used for such passive transdermal delivery (e.g., for transdermal delivery of acetylcholine);

the present invention provides methods and apparatuses for achieving a local (non-remote, non-systemic) microvascular effect of transdermal preparation;

the present invention provides mechanisms for monitoring the effect of the application of the micro-patches; and the present invention provides for testing and applying varying concentrations of agent, including concentrations much greater than those used for standard care with the given agent. This is possible because the micro-patch limits total dosages and hence systemic and remote drug levels. Any adverse local effects from high doses would readily be detected by real-time monitoring.

Referring to FIG. 1, a system for implementing the present invention entails the application and positioning of a probe 1 (shown here as a laser Doppler flowmetry but also could be an alternative monitoring device such as a laser Doppler scanner, laser speckle or photoplethysmograph) above a micro-patch 2 with a transparent or translucent backing 3. As shown in FIG. 1, the patient end 4 of the laser Doppler flowmetry probe 1 is enclosed in, and supported by, a probe holder 5. One of the potential alignments in accordance with a preferred embodiment of the present invention, as shown in FIG. 1, entails attachment of a first side 6*a* of a double-sided adhesive ring 6 (or comparable double stick interface) to the probe holder 5 and the other, or second, side 6*b* of the double-sided adhesive ring 6 to the top surface 2*a* of the translucent micro-patch 2 with desired agent.

Figure 2:
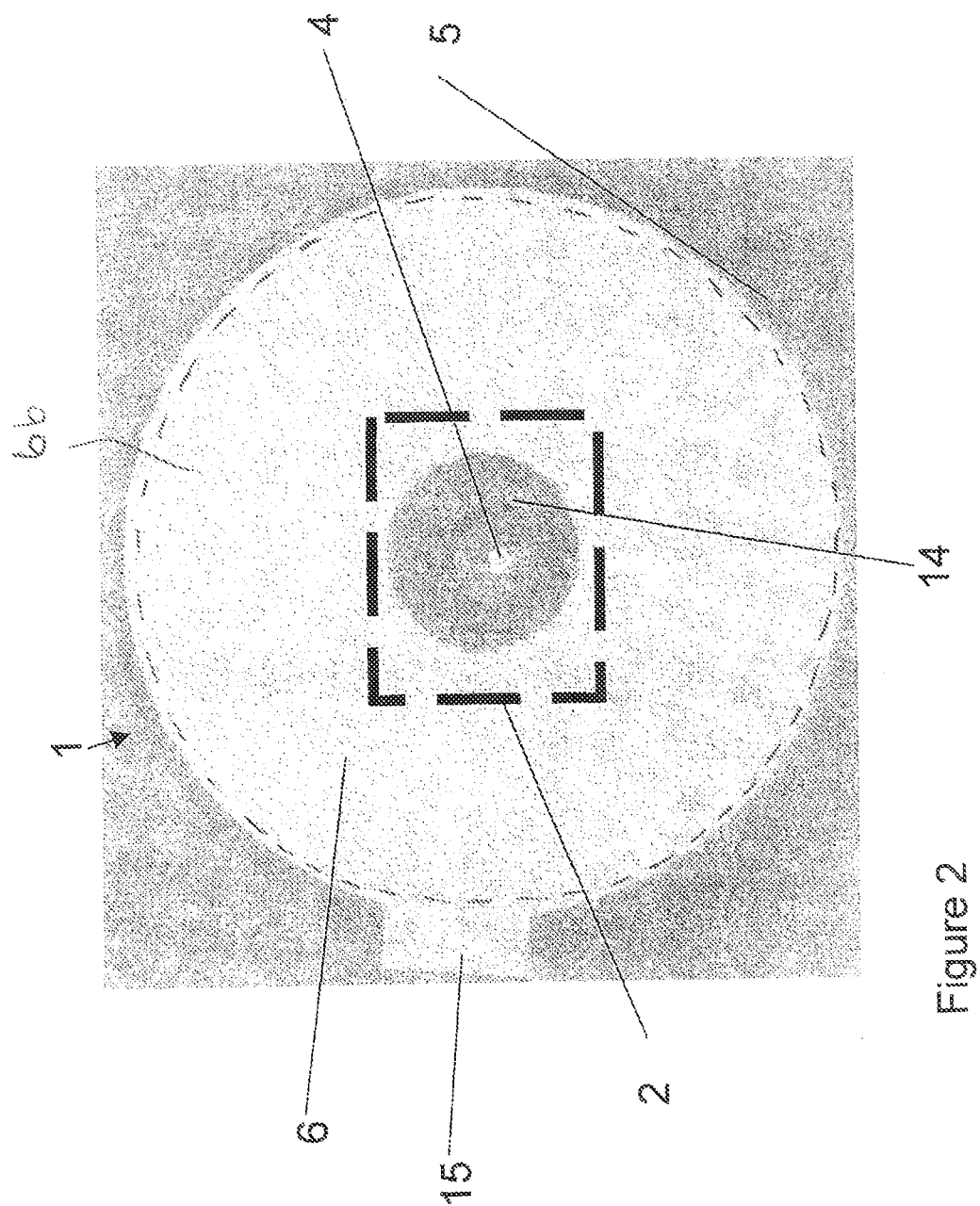
FIG. 2 is a plan view from below the end of an alternate embodiment with a probe (laser Doppler flowmetry probe), micro-patch (shown by broken lines as it is transparent and covered by the double-sided adhesive ring), and double-sided adhesive ring (whose patient surface remains covered). In accordance with a preferred embodiment, the micro-patch (rectangle outlined with broken line) is slightly larger than the desired delivery area; it therefore is placed between the encased laser Doppler flowmetry probe and the double-sided adhesive ring such that the rim around the ring opening controls the area of drug exposure.

In accordance with a preferred embodiment of the present invention, and as shown with reference to FIG. 2, the first side 6*a* and second side 6*b* of the double-sided adhesive ring 6 are provided with cover members 15 (only shown attached to the second side 6*b* in FIG. 2), which are selectively removed from the double-sided adhesive ring 6 when desired for use in accordance with the present invention. The cover members 15 help protect the double-sided adhesive ring 6 from inadvertently sticking to anything prior to attachment to the probe holder 5 and the micro-patch 2. The micro-patch 2 and double-sided adhesive ring 6, which as shown in FIGS. 1 and 2 extends beyond the periphery of the micro-patch 2, both may contain adhesive, are ultimately attached to the surface 7 of the tissue 8 under study. The adhesive in the micro-patch 2 can be mixed with the agent(s) to be delivered or in agent-free zones.

FIG. 2 is a view from below which illustrates a slight modification of the embodiment shown with reference to FIG. 1, that is, the order of the micro-patch 2 and double-sided adhesive ring 6 are switched such that the micro-patch 2 is positioned between the probe 1 and the double-sided adhesive ring 6. Light is shown emerging from the distal end (or patient end) 4 of the laser Doppler flowmetry probe 1 in its probe holder 5. In the embodiment shown in this figure, the micro-patch 2 is larger than the actual site of measurement; therefore, its area of delivery is limited by a mechanism such as the double-sided adhesive ring 6, with a central opening 14. More particularly, the micro-patch 2 is positioned between the probe 1/probe holder 5 and the double-sided adhesive ring 6 with the ring 6 creating a barrier between the micro-patch 2 and the study surface 7 where contact between the micro-patch 2 and the study surface 7 is limited to the area permitted by the central opening 14 formed in the ring 6. The adhesive patient surface of the double-sided adhesive ring 6, and micro-patch 2, can be applied to the study site after its cover member 15 is removed.

As various micro-patch embodiments are described herein, similar reference numerals will be used to designate similar components of these various embodiments. In accordance with a preferred embodiment(s), the drug-containing micro-patch 2 is a quantifiable thin layer of a transdermal preparation, preferably in the form of an individual button-sized unit (typically approximately 0.25 cm to approximately 2.5 cm diameter, tailored to the size of the site to be monitored), a peel-away button-sized unit from a larger strip, or a button-sized punch-out from a larger patch. The dose of agent applied to the study surface 7 by the micro-patch 2 will be low enough to preclude the potential for significant systemic levels of drug as may be confirmed by measurement of blood levels, systemic effects or changes at a remote site (unless one deliberately selects a dose that enables detection of systemic or remote effects). For each drug/vehicle combination, the minimally effective dose and maximum non-systemic dose may be determined in dose-response studies as would typically characterize introduction of a new drug or new means of delivery.

Whereas prior art patches and other forms of agent delivery are designed to accelerate initial delivery of drug, preferred embodiments of the present invention seek to delay initial delivery so as to enable attainment of baseline data. In order to permit assessment of baseline and post-drug states without the need to move the monitoring probe, that is, the laser Doppler flowmetry probe in accordance with a preferred embodiment of the present invention, preferred embodiments of the micro-patch 2 may delay delivery of the drug or agent. For example, and as discussed below in greater detail, in accordance with a preferred embodiment of the present invention, the delivery of a nicotine micro-patch 2 is delayed for 10-20 minutes by placing a commonly applied translucent dressing (e.g., a TEGADERM™) beneath the micro-patch 2. As shown in FIG. 3, this is achieved by constructing the micro-patch 2 with an inert layer, such an inactive matrix 32, or a rate-controlling film on the patient side of the active layer 34. Referring to FIG. 4, delayed delivery of the drug or agent is achieved by constructing a micro-patch 2 with the drug encapsulated in a carrier vehicle 38, such as, dissolvable or destructible capsules. In addition, it is contemplated the delayed delivery of drug may be achieved by altering solubility as by interaction with a "linker," or conversion of an inactive to active ingredient. In particular, the micro-patch 2 as shown in FIG. 3 includes layers progressing from a clear (or transparent) backing 3, to the study agent to be delivered 34, to an inactive layer/matrix 32 that can be customized to delay delivery of the drug, to a protective cover member 36 that is removed just prior to application of the micro-patch 2 to a subject. The micro-patch 2 shown in FIG. 4 includes layers progressing from a clear backing 3, to the drug encapsulated in a carrier vehicle 38 to delay its delivery, to a protective cover member 36 that is removed just prior to application of the micro-patch 2 to a subject. With regard to the embodiment described above with reference to FIG. 1, the clear backing 3 is secured to the double-sided adhesive ring 6 for attachment to the probe holder 5 while the inactive layer/matrix 32 or the drug encapsulated in a carrier vehicle 38 is oriented for placement directly upon the study surface 7.

Figure 5A:
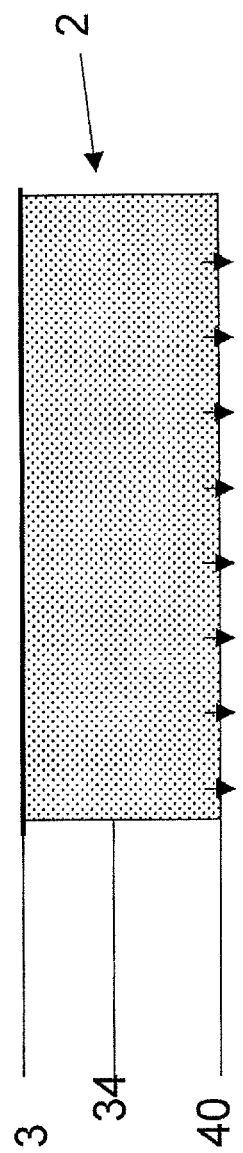
FIG. 5A is a schematic of an alternate embodiment showing a micro-patch with projections directed toward the skin so as to increase drug penetration. The projections may be solid or hollow microtubules.
Figure 5B:
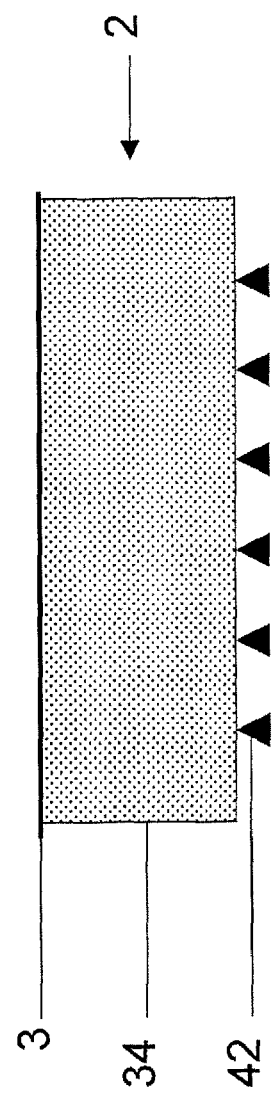
FIG. 5B is a schematic of an alternate embodiment showing an inventive array of projections—directed toward the micro-patch—so as to convert the micro-patch from baseline to drug delivery states. As with the embodiment shown with reference to FIG. 5A, the projections may be solid or hollow.

Additionally, and with reference to FIG. 5A, the micro-patch 2 is provided with drug-coated mini-projections 40. This embodiment utilizes drug-coated mini-projections 40, for example, those provided by of Alza Corporation's Maxroflux® Transdermal Technology, to create superficial pathways through the skin's dead barrier layer allowing transport of macromolecules via micro-patch 2. As with the prior embodiments, the micro-patch 2 includes layers progressing from a transparent backing 3, to the drugs contained in the active layer 34, to the mini-projections 40 permitting delivery of drugs contained in the active layer 34. FIG. 5B illustrates an inventive modification of the miniprojection technology, such that reverse projections 42 extend into the micro-patch 2 to open up channels for agent delivery and/or dissolve capsules or other means that have delayed drug delivery (e.g., to allow mixing of acetylcholine and water). As with the embodiment disclosed with reference to FIG. 5A, the micro-patch 2 includes layers progressing from a transparent backing 3, to the drugs contained in the active layer 34, to the reverse projections 42 permitting delivery of drugs contained in the active layer 34.

The present invention introduces a 2-step process for the mini-projection technology, wherein the first step involves placing the micro-patches 2 gently on the study site surface and the second step entails initiating (or markedly increasing) delivery upon advancement of the monitoring probe 1. The apparatuses and methods to achieve this are described below with reference to FIGS. 11-14 that are discussed below in greater detail.

Figure 6:
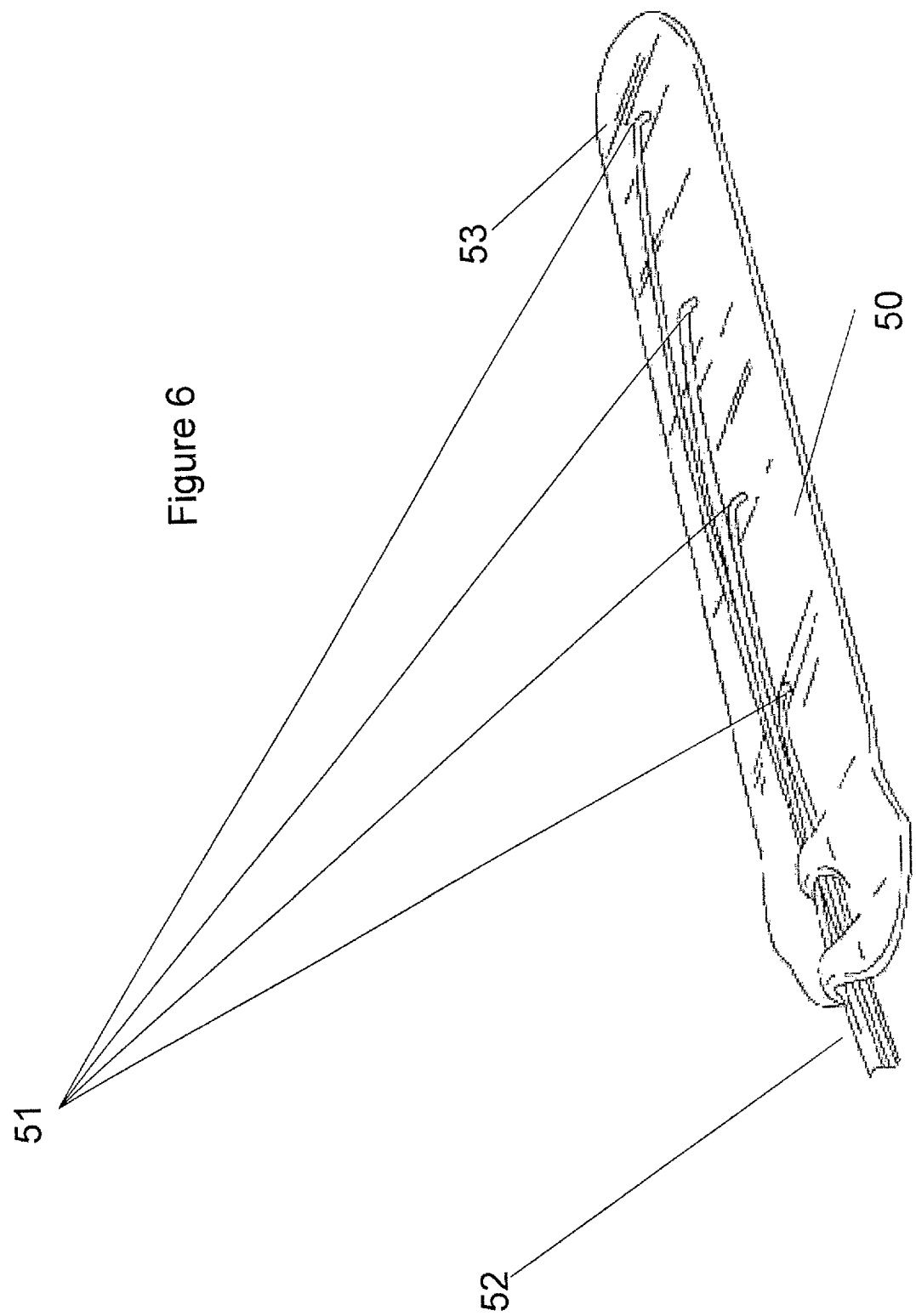
FIG. 6 is a perspective view of an alternate embodiment showing a patch in the form of strip with "micro-patches" at the end of microfibers to enable persistent monitoring of one of more micro-patch sites (e.g., laser Doppler flowmetry, photoplethysmography, tracer or substrate transfer) and consistent positioning sites while the patch is in place.
Figure 7:
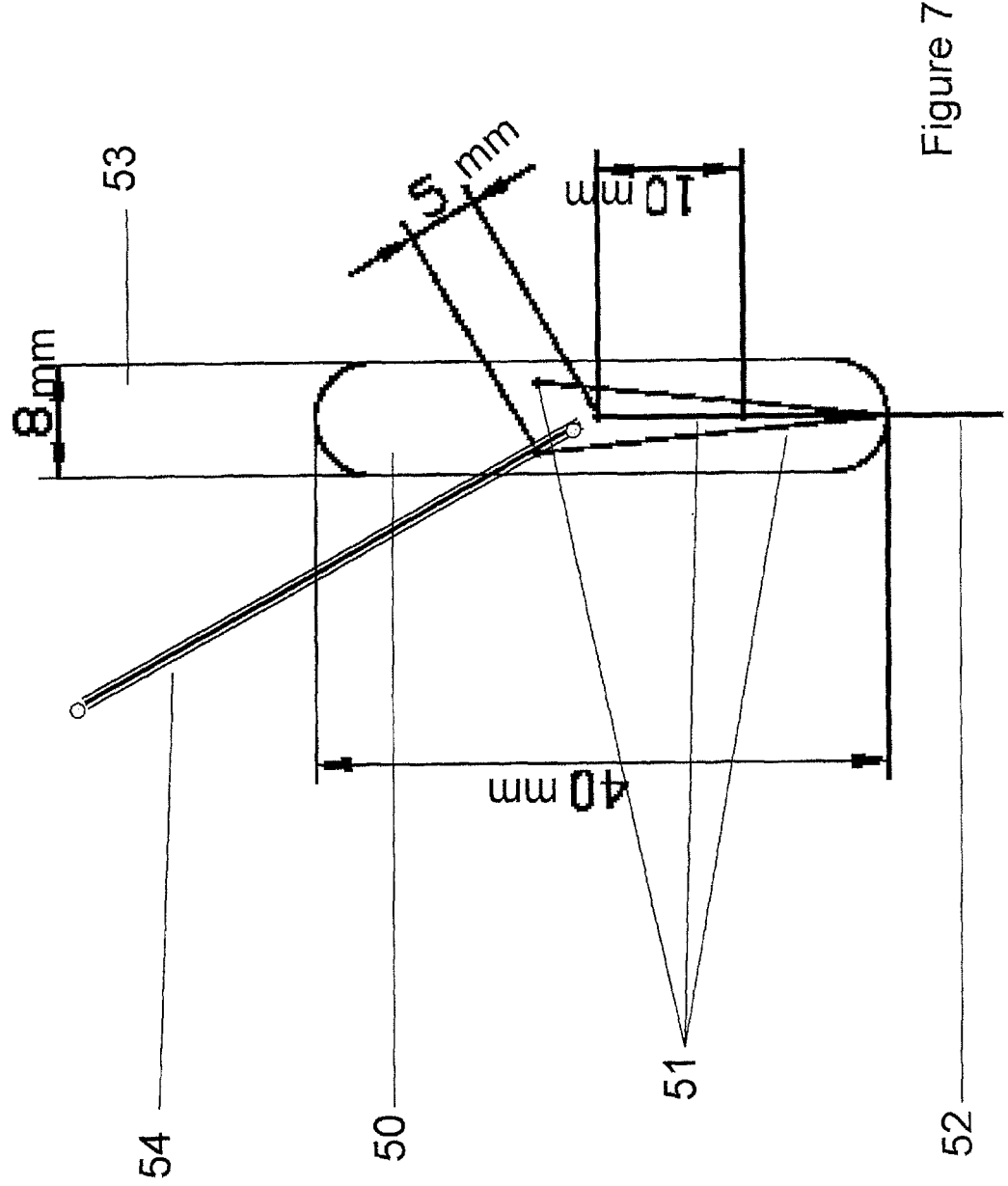
FIG. 7 is a schematic of an alternate embodiment showing a micro-patch with microfibers in an alternative pattern and also demonstrates how a similar channel may be used to deliver agent to one or more microfiber monitoring sites and/or sample fluid for direct assessment of tracer of substrate in underlying interstitium; as per FIG. 6, a portion of the of the strip anchors the strip in place.

An alternative micro-patch 2 configuration is shown with reference to FIGS. 6 and 7. The prior art includes mechanisms to embed microfibers within or below a plastic strip before directing downward for implantation on the brain surface. The present invention adapts that technology to the inventive micro-patch. In accordance with a preferred embodiment of the present invention, a typical plastic strip 50 is customized to include light-transmitting fibers 51 (approximately 0.25-0.45 mm diameter in accordance with a preferred embodiments) in a desired array (for example, four fibers as shown with reference to FIG. 6, three fibers as shown with reference to FIG. 7) for use in monitoring the microcirculation. The microfibers are grouped in a bundle as they leave the strip 50 for connection to separate laser Doppler channels e.g., four laser Dopplers and photoplethysmographs, sensors for tracer and/or substrate). In accordance with preferred embodiments, the strips 50 themselves are constructed in the form of the micro-patches 2, as illustrated in FIGS. 1, 3, 4, 5A and 5B (with the addition of light transmitting fibers as discussed above), and deliver study agent to a study site. The micro-patches need not be translucent. The embedded microfiber construction offers another potential advantage: it can be anchored (e.g., with adhesive) at one end 53 so that, after baseline readings are obtained, a portion of the strip 50 can be lifted to enable application of a micro-patch 2 at one or more study sites and then replaced without causing a shift in microfiber orientation (and thus constitute one of several ways described in the present disclosure to minimize the impact of spatial heterogeneity). FIG. 7 introduces another potential feature of several embodiments: an embedded microtubule 54 for infusion of agents and/or withdrawal for measuring tracer or substrates.

Figure 8:
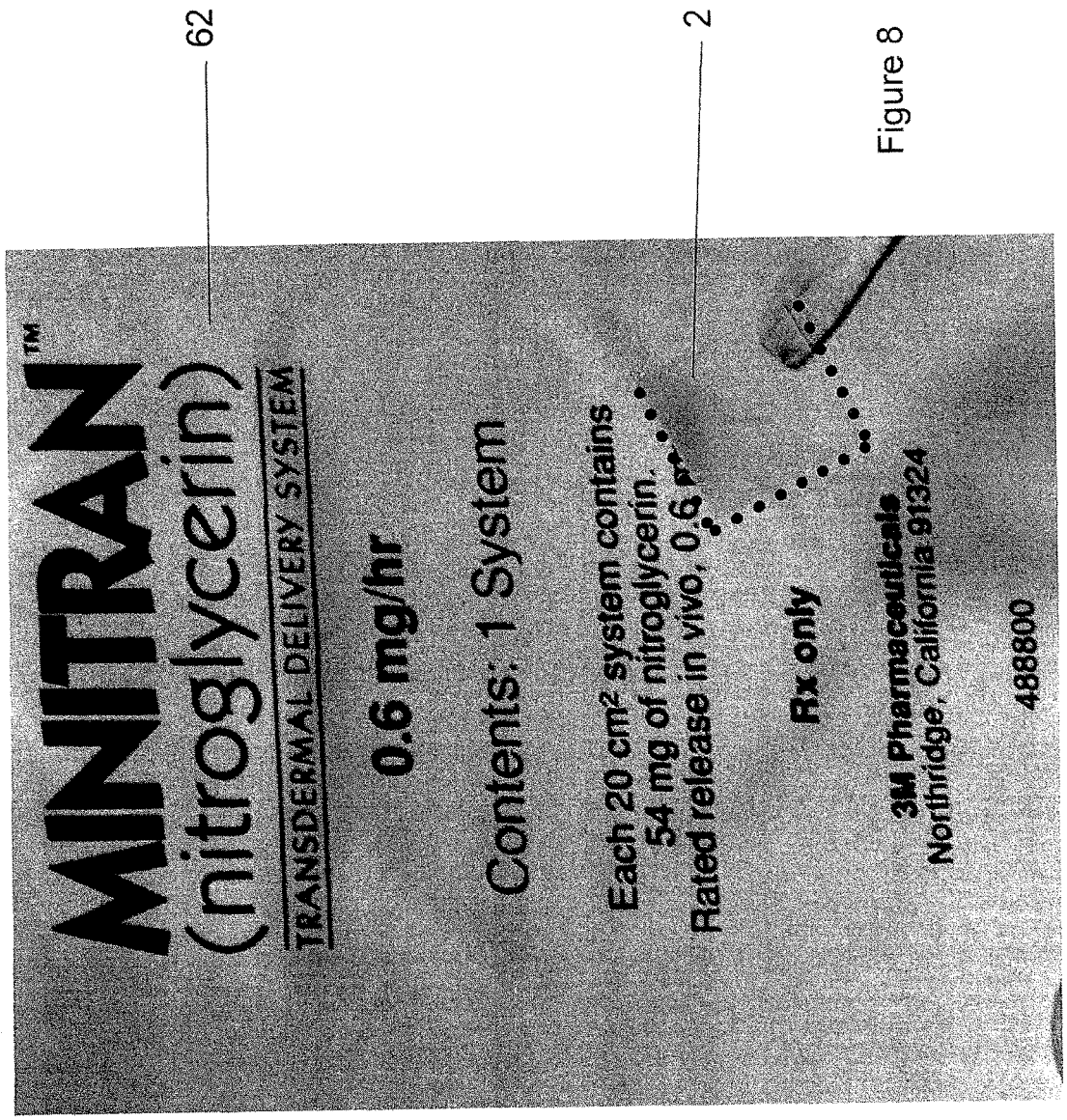
FIG. 8 is a front plan view photograph showing the size of a nitroglycerin micro-patch in accordance with the present invention compared to a package containing a full-size patch. The rectangle shown here enables monitoring over an area greater than that covered by a standard stationary probe. For a stationary probe, a button-shaped micro-patch typically is sufficient.
Figure 9:
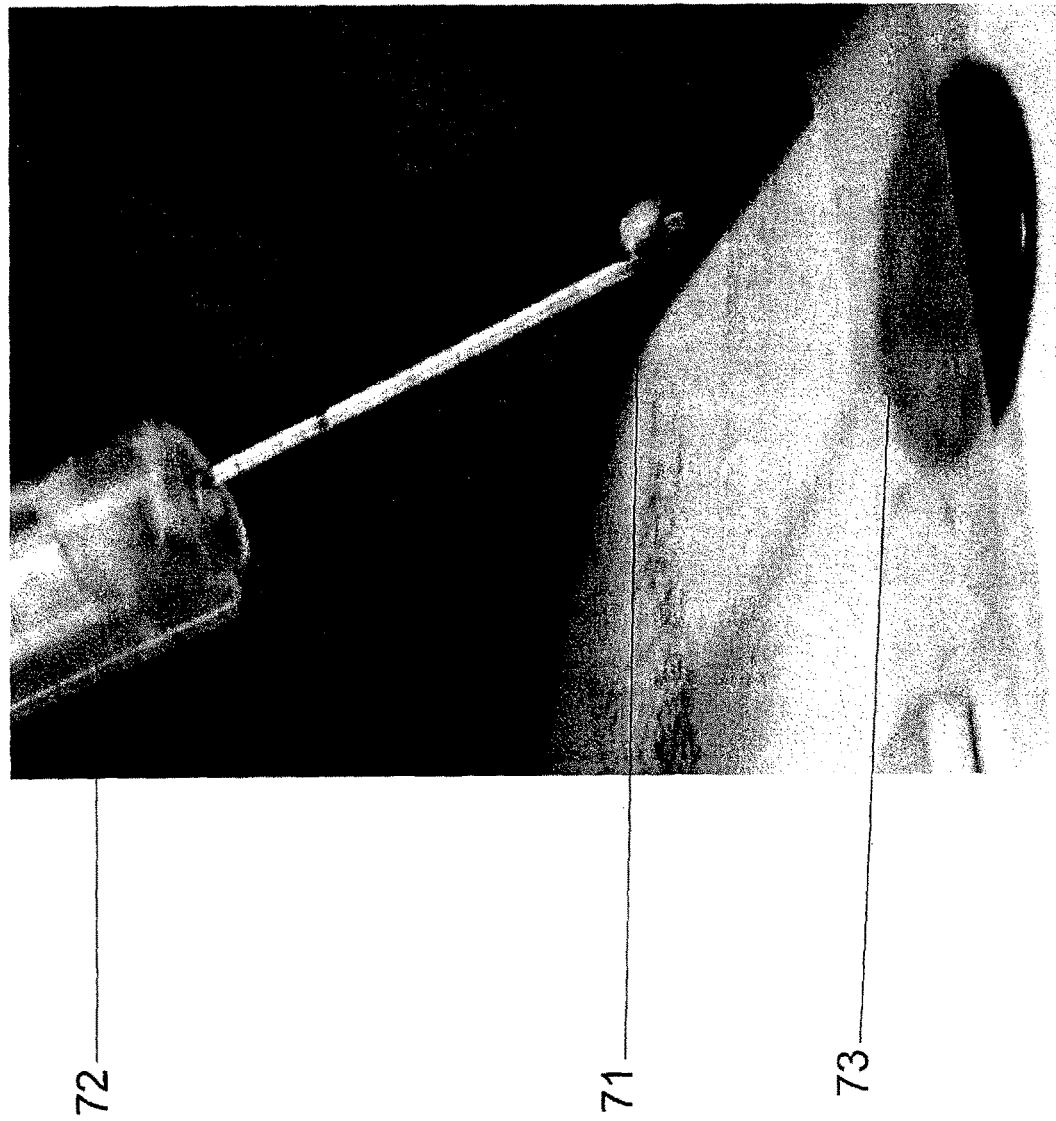
FIG. 9 is a perspective view photograph showing delivery of an aliquot of acetylcholine dissolved in water from a calibrated syringe (held in hand) to translucent tape to prepare an acetylcholine micro-patch in accordance with the present invention.

Two embodiments of micro-patches 2 in accordance with the present invention are shown in FIGS. 8 and 9. FIG. 8 shows the size of a nitroglycerin micro-patch 2 compared to a package 62 containing a full-size conventional patch. The rectangle shown here enables monitoring over an area greater than that covered by a standard stationary probe. For a stationary probe, a button-shaped micro-patch 2 typically is sufficient. FIG. 9 shows delivery of an aliquot of acetylcholine dissolved in water 71 from a calibrated syringe (held in hand) 72 for deposition on translucent double-stick tape 73 to prepare an acetylcholine micro-patch.

In addition to the various embodiments described above, it should be appreciated that multiple potential variations of micro-patches are contemplated for use in accordance with the present invention. FIGS. 10A to 10D shows how a small section 81 can be removed to create an opening 82 as a drug-free zone or for introduction of a second agent or to enable direct application of a monitoring probe 83. The multiple opportunities for evaluating drug interaction become evident when embedded microtubules 54 for infusion of agents and such an opening 82 are included in the same micro-patch 2. More particularly, FIG. 10A shows the opening 82 in the micro-patch 2. FIG. 10B shows how monitoring can be accomplished via the opening 82 through utilization of a monitoring probe 83 secured to the micro-patch 2 at the opening 82. FIGS. 10C and 10D show how drug delivery may be accomplished not only by simply applying drug via the opening 82 but also via microtubules 54 which enable delivery to the opening 82 as well as to other areas beneath the micro-patch 2.

Figure 11:
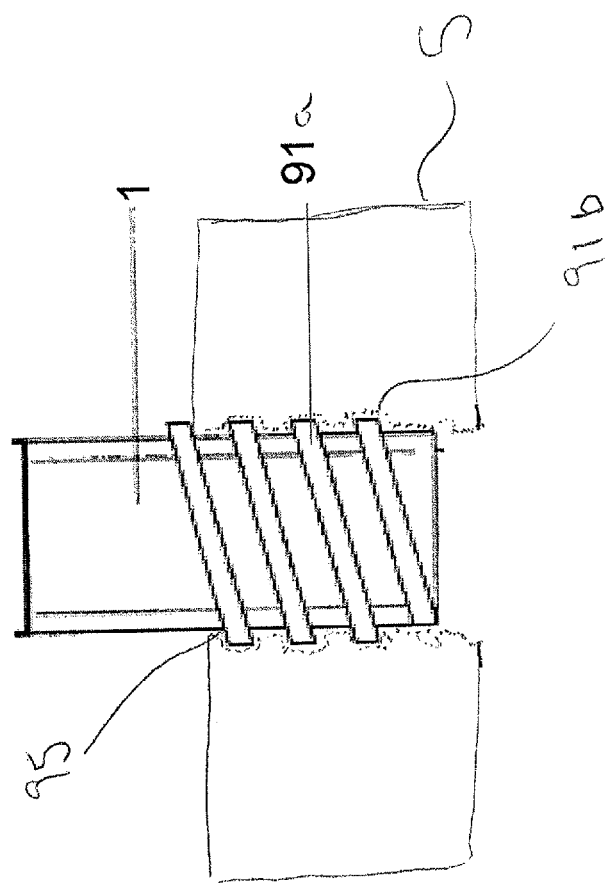
FIG. 11 is a plan view of a schematic showing a probe (for laser Doppler flowmetry) and probe holder with threading for advancing the laser Doppler flowmetry probe, or alternative monitoring device, within a holder adherent to skin by a screwing mechanism for threaded engagement. This arrangement and modifications such as those shown in FIGS. 12, 13 and 14 enable probe advancement so as to activate delivery of agent by the micro-patch (after baseline), and/or enable deliberate rotation of a probe so as to sample multiple sites without having to remove and replace the probe (especially if a probe with multiple channels is used) and, when desired, may further limit probe mobility.

In addition to the simple mechanisms for micro-patch application and adhesion and associated monitoring device interaction described above and illustrated in FIGS. 1, 2, 6, 7, and 10, in selected embodiments, secured advancement of a laser Doppler flowmetry probe or alternative monitoring device may be accomplished by one of several mechanisms of interaction and advancement. This process may offer the advantage of further limiting undesirable monitoring probe mobility and enables monitoring probe advancement so as to activate delivery of agent by the micro-patch 2. FIG. 11 shows a probe 1 and probe holder 5. The probe 1 includes threads 91 on an external surface thereof. The external threads 91a of the probe 1 are shaped and dimensioned for engagement with internal threads 91b formed along a cavity 95 of the probe holder 5. In this way the probe 1 may be adjusted relative to the probe holder 5 by simple rotation of the probe 1 relative to the probe holder 5.

FIG. 12 shows an alternate embodiment. As with the embodiment disclosed with reference to FIG. 11, the probe 1 includes threads on an external surface thereof. The threads of the probe 1 are shaped and dimensioned for engagement with internal threads formed along a cavity of the probe holder 5. The probe holder 5 is provided with a lower recess 96 including internal threads 97 on the inside of the lower recess 96 of the probe holder 5 for engagement with matched external threads 98 on a probe-to-study site coupler 92 upon which the micro-patch 2 is mounted for supporting the micro-patch 2 adjacent the study site. Advancement of the probe 1 by rotation of the probe holder 5 relative to the probe-to-study site couple 92 applies pressure to the micro-patch 2. While this may achieve drug delivery simply by increasing micro-patch 2 adherence to the study surface, it may also serve to advance drug-coated miniprojections when a micro-patch 2 such as those shown in FIGS. 5A and 5B is employed in accordance with the present invention.

In accordance with a preferred embodiment of the present invention, the present system has a baseline setting which fixes the probe without pressure on or just above the micro-patch and a second position which applies enough pressure to activate drug delivery. The pressure may remain for the duration of monitoring or one may return to the baseline position for subsequent monitoring. The process introduces another important feature for preferred embodiments in accordance with the present invention: if a multi-channel probe is used, it can be turned in calibrated increments so that multiple sites can be monitored without having to remove and replace the probe. While this contemplated technique may be accomplished using a variety of support structures, FIG. 13 presents a schematic of an exemplary support structure including a laser Doppler flowmetry probe 1 in a probe holder 5. The probe 1 is advanced and secured in position by luer-lock engagement of matched projections and grooves 100a and 100b herein respectively shown on the inner surface of lower recess 96 of the probe holder 5 and outer surface of the probe-to-study site coupler 92. This is accomplished by deliberate turning of the probe 1 and its probe holder 5. The micro-patch 2 is located in the coupler 92 and is pushed forward toward the study surface by probe 1 advancement via the threaded engagement of the probe 1 and probe holder 5 as discussed above with reference to FIG. 11.

FIG. 14 is a schematic showing a laser Doppler flowmetry probe 1 wherein the light guide fiber(s) is separated from the study surface by a spring 111 within the probe holder 5. The spring 111 resiliently supports the probe 1 within the probe holder 5 allowing for controlled movement of the probe 1 relative to the probe holder 5. After baseline readings are obtained with the micro-patch 2 lying gently on the study surface, the laser Doppler flowmetry probe 1 is advanced downwardly toward the study surface transiently compressing the spring 111 and increase adherence of the micro-patch to the study surface. In accordance with a preferred embodiment, it is contemplated the probe will be coupled to the micro-patch through the utilization of a probe-to-stud site coupler as discussed above with reference FIGS. 12 and 13.

Multiple alternatives for comparable engagement and disengagement previously have been described by the inventor, with respect to engaging needles and diaphragms, in U.S. Pat. No. 6,391,014, which is incorporated herein by reference. It is contemplated, these engagement and disengagement mechanisms may be employed within the spirit of the present invention. Although the basics of preferred techniques are disclosed above in accordance with a preferred embodiment of the present invention, those skilled in the art will appreciate a variety of mechanisms may be employed for facilitating movement of the probe, including probes for laser Doppler flowmetry, photoplethysmography and/or quantify tracer and/or substrate.

In addition to embodiments where a single channel probe contacts the study surface or simply is separated from surface by the micro-patch and possibly adhesive, the present invention provides various embodiments that provide a persistent gap between the monitoring probe and the underlying tissue. Spatial heterogeneity under the probe may be mitigated by use of an integrating multichannel probe, a commercial version of which (from Perimed, Sweden) has seven closely packed channels that emit from a single source and return the signal to a single detector. The use of such a probe in a fixed position reduces but does not eliminate the effect of spatial heterogeneity. In considering this problem the present invention adopts two modifications that are described below:

A multi-channel probe 1 with independent channels confidentially customized to predetermined specifications. Each channel is independently aligned with a detector (e.g., for assessment of Doppler shift, absorption of photoplethysmographic signal, or assessment of tracer or substrate concentration. In the embodiment shown in FIG. 15, three channels 121 are interfaced to a common laser light source such each of these independent channels 121 transmits light to the distal end of the probe 1, which is shown being mounted in a standard probe holder 5; each interfaces with a separate sensor.

Mounting the probe in a special holder that enables precisely repositioning the probe above the study site (s). FIG. 16 shows an inventive probe support assembly 131 for mounting a probe 1 (in this case a multichannel probe with a widened distal end) above the skin. The support assembly 131 is designed to enable consistent movements in fixed increments (e.g. 1 mm) so as to obtain new measurements without disturbing the alignment of the probe 1 with the skin or an underlying micro-patch 2. Movements are generated by a sliding bar 132 in horizontal and vertical directions in accordance with a visible grid 133. This new, movable, probe support assembly 131 was engineered so that the integrating probe 1 would be suspended a couple of millimeters above the study site 7 on the forehead, with the ability to be moved at fixed intervals in a two dimensional fashion. More specifically, it typically enables measurement of blood flow in a 1 cm×1 cm area on the forehead by obtaining multiple different readings in this area, with reading points distributed approximately 1 mm apart in a grid-like pattern. Using this probe support assembly 131 a significant decrease in the influence of spatial heterogeneity has been noted. Additionally, by rotating the probe 1 in approximately 30 degree increments, a second and third set of seven readings may be acquired without any probe 1 displacement or micro-patch 2 disturbance. This may be facilitated by use of tabs or related means to regulate the degree of rotation.

More particularly, and with referring once again to FIG. 16, the probe support assembly 131 includes four legs 134 extending downward for engagement with the subject, for example, the forehead 7 of the patient being treated. The engaging ends of the legs 134 are provided with adhesive pads 135 for secure attachment to the forehead. The legs 134 are threadingly engaged with the base structure 136 in a manner permitting relative adjustment. The slide arm 132 includes a coupling structure 137 for attachment of the probe 1 thereto in a manner such that the probe 1 is focused upon the forehead of an individual in a desired manner. As a result, one may move the slide arm 132 relative to the base structure 136 in a controlled and efficient manner. As shown with reference to FIG. 16, a micro-patch 2 is selectively placed under the probe 1 while it is held in this elevated assembly.

The size of the area that should be encompassed by a moving probe (or scanner) to capture areas of microvasculature that are close to as well as distant from the feeding arteriole, will depend on the region one is studying and should be based on evidence. This may be obtained by performing local biopsies to determine the distance between arteriolar-capillary networks or by mapping with a laser Doppler to determine the distance between peak values and then determining the distance that is required to ensure that the peak will be maintained in an acceptable number of patients (e.g., 95%, which may be obtained by 2 standard deviations). The inventor and his colleagues have compared laser Doppler readings to histological preparations from skin biopsies on ourselves and thereby gained an appreciation of the forearm microvasculature. [Braverman I M, Schechner J S, Silverman D G, Keh-Yen A: Topographic mapping of the cutaneous microcirculation using two outputs of laser-Doppler flowmetry: flux and the concentration of moving blood cells. Microvascular Research 44(1):33-48, 1992 July]. The application of mapping data will be limited by the size of the probe that can be comfortably and effectively placed and moved on the skin as well as on the acceptable size of micro-patch (so that only local effects are produced).

It is contemplated the benefits of a multichannel probe may be achieved with other configurations than the seven channel probe as shown. So long as cross-talk among fibers is minimal, they can be packed closely together and in different configurations. Individual probes also can be arrayed to sample an area of tissue. Spacing can be optimized to ensure maximum site coverage when the probe is rotated (as described above). It should be noted that, although the introduction of a multi-channel probe in accordance with the present invention is primarily for assessment at sites of transdermal application, the probe also is applicable to other types of challenges.

In its simplest form, the disclosed mechanism of monitoring perfusion does not require a computer, since one primarily is assessing increases in blood flow'or the amount of tracer or substrate. However, it would be helpful to be able to delineate the time course of the response and to analyze potential changes in the oscillatory patterns of flow with computer-based algorithms. Embodiments which entail simultaneous recording of multiple inputs and/or frequent serial measurements obviously benefit from computerized acquisition (as described herein). Specifically, among the indices that can be monitored in accordance with the present invention are:

Absolute or percent changes in flow or volume or tracer transfer or blood component (e.g., substrate) transfer (and/or comparable measures of microvasculature status and function including:
"drug phase/baseline" or
"(drug phase-baseline phase)/baseline".
Time course of changes in flow or volume or tracer transfer or substrate transfer (and/or comparable measures of microvasculature status and function) including:
Changes in pulse wave associated with individual heartbeats;
Changes in oscillatory patterns, as the inventor and others have been shown to be indicative of cholinergic oscillatory and/or adrenergic control of the; microvasculature. [Silverman D G, Stout R G: Distinction between atropine-sensitive control of microvascular and cardiac oscillatory activity. Microvasc Res 63:196-208, 2002;];
Changes in local vs. systemic values; and
Changes in lag time between changes in concentration of tracer or substrate in blood vs local site.

U.S. patent application Ser. No. 12/059,383 discloses evaluations of transdermal application of nicotine, nitroglycerin, estrogen, scopolamine (from existent large patches) as well as acetylcholine (micro-patch solution prepared in accordance with the present invention from acetylcholine powder) and phenylephrine (prepared in accordance with the present invention from existent solution). Since acetylcholine (as well as phenylephrine) had not previously been delivered transdermally, the efficacy thereof was tested with respect to doses, concentrations, vehicles and time-courses. This led to a preferred embodiment for delivery of this agent in a manner that enables drug delivery and concurrent microvascular monitoring.

A preferred embodiment of the present invention entails the use of acetylcholine, since this agent is well-suited for testing of the integrity of the microvasculature. The use of this agent in a micro-patch offers the unique advantages, including: a) acetylcholine is an endogenous vasodilator that is sensitive to disorders of the endothelium lining blood vessels; and b) acetylcholine has a brief half-life, such that it is rapidly metabolized and hence, when administered as a micro-patch, has minimal systemic effects. These features have prompted the preparation for conducting trials with succinylcholine, a drug that mimics the effect of acetylcholine at many receptors; it offers the added feature of prolonged residence and rapid metabolism since it is not metabolized at the tissues but by plasma cholinesterase in the blood. Trials with acetylcholine included multiple potential diluents with a range of hydrophilicity (vs hydrophobic) and translucency:

Ointments—oleaginous in nature
Creams—oil/water and water/oil emulsions
Gels—suspensions interpenetrated by a liquid Mixing was accomplished to achieve a final product that was smooth and free of abrasive particles. Based on trial and error testing, it was elected to pursue testing with acetylcholine chloride powder dissolved in water for placement on an adherent surface (e.g., clear tape). This led to a preferred embodiment of an acetylcholine micro-patch wherein acetylcholine solution is prepared by mixing 100-mg of acetylcholine chloride (Spectrum Chemical; New Brunswick, N.J.) with 0.6-mL high pressure liquid chromatography (HPLC) grade water to a final volume of 0.7-mL and molar concentration of 786.4 M. Then, as shown in FIG. 9, 0.02-mL (2.8 mg) of this concentrated acetylcholine solution 71 was spread on a translucent backing; originally a section of double-stick tape 73 but, more recently a commercially available double-stick clear disk (diameter 12.6 mm, area 124.7-mm$^2$) otherwise used for attaching two items but not for development. of the inventive micro-patch. This dose is proportional to doses of MIOCHOL-E,™ (that is, a clinically available acetylcholine preparation that is used to produce papillary constriction (miosis) during cataract surgery) that had been tested in preliminary trials. However, the agent used for micro-patches can be superconcentrated compared to the solution used for intraocular injection— made possible because of the small delivery area.

The dry side of the acetylcholine "micro-patch" was adhered to the end of a laser Doppler flowmetry probe (a PF 5010 with Probe Model 407, Perimed, Sweden in accordance with a preferred embodiment) (see FIGS. 1 and 2). A sham drug micro-patch was made in the same way with 0.02-mL of HPLC-grade water instead of acetylcholine solution. Before micro-patch application, a DOUBLE-STICK DISC™ (3M Health Care, Neuss, Germany) (that is, the double-sided adhesive ring 6 discussed above) with an overall diameter of 38.1-mm and a central hole (or opening) diameter of 8.7-mm is placed at the site to be tested. The double-sided adhesive ring 6 serves as an adherent base onto which a monitor such as a laser Doppler flowmetry probe 1 is placed as well as to define the area (59.4-mm$^2$) for drug application. In addition to providing for targeted adherence, when placed between the micro-patch 2 and the study surface (as shown in FIG. 1) this further limits the area of drug delivery by providing a barrier to drug delivery from the outer regions of the micro-patch 2. As detailed below, this delivered as much as 10% of that used to constrict the pupil during cataract surgery Dose-response curve can be assessed with serial dilutions. As shown in Table 2, other investigators have used a dose twice that employed in the present study. Laser Doppler flowmetry is an exemplary form of potential monitoring (used in each of the Table 2 studies).

Table 2 compares the findings with transdermal application of acetylcholine in accordance with the present invention to those with iontophoresis in order to confirm that non-iontophoretic transdermal delivery (introduced herein) is effective:

the section used in the inventive micro-patch delivered at a rate of approximately 0.008-mg/hr. Although not currently available, lesser or higher concentrations of nitroglycerin may be used for micro-patches, pending dose response studies to confirm local efficacy and lack of systemic effects. The nitroglycerin micro-patch then is placed onto a double-sided adhesive ring for adherence to a monitoring probe (see FIGS. 1 and 2) or it may be placed on the tissue under an elevated support assembly 131 or scanner (described below).

Prior to the customization of nitroglycerin according to the present invention, nicotine was customized in accordance with the purposes of present invention. This entailed customization of a commercially available clear NICODERM patch, nicotine delivery patch, (with 0.83 mg of nicotine/cm$^2$). Again, lesser or higher concentrations may be used for a micro-patch; these are not currently available, since currently available nicotine patches delivery a fixed dose/cm$^2$ patch such that a higher systemic dose is obtained by using a larger patch.

The design of other transdermal preparations entailed processes similar to that for acetylcholine, nitroglycerin and nicotine. Likewise, scopolamine micro-patch was prepared from a patch wherein delivery of systemic level is used to treat nausea. Transdermal phenylephrine was prepared by trial and error application of different concentrations and volumes of the drug as per acetylcholine. Subsequently, micro-patches for estrogen and rivastigmine were designed from a full-sized patch; the latter, which likewise adhered to

TABLE 2

Comparison of responses to Acetylcholine

| Technique | Investigator | Approx Amount of Acetylcholine | Change in Blood Flow | Reference |
|---|---|---|---|---|
| Iontophoresis Forearm | Noon | 0.25 ml of 2% | 1000% inc | Br J Clin Pharmacol 1998;45:545-50 |
| Iontophoresis Forearm | Morris | 0.25 ml of 1% | 50-100% inc | Diabetologia 1995;38:1337-44 |
| Transdermal Forehead | Silverman | <0.25 ml of 1% | 50-250% inc | Data presented herein |

The creation of a nitroglycerin micro-patch so as to enable concurrent monitoring of an endothelium-dependent transdermal preparation (acetylcholine, described above) and an endothelium-independent vasodilator (nitroglycerin) is simpler than the creation of the acetylcholine micro-patch. As illustrated in FIG. 8, a disclosed embodiment entails the conversion of a full size patch (shown with reference to package 62) to a micro-patch 2 that is adhered to the skin and adapted for monitoring as per acetylcholine above. The present invention provides not only for the application of the disclosed method for monitoring the local circulation but the tailoring of the micro-patch to ensure effective delivery throughout the monitoring site while avoiding delivery of excess drug that might predispose to remote and/or systemic effects. For a single laser Doppler flowmetry probe, the nitroglycerin micro-patch may be obtained by using a standard hole-punch to cut a 6-mm diameter (28.3-mm$^2$ area) section of a full size 0.6 mg/hr MINITRAN™ nitroglycerin patch (3M, Minnesota). Alternatively, for applications where one wishes to move the laser Doppler flowmetry probe so as to encompass a larger area (as with the inventive assembly in FIG. 16), a small rectangle may be appropriate. Such patches are designed for homogeneous delivery of drug at a rate of 0.03-mg/hour per 100-mm$^2$ area of patch, such that the objectives of Table 1, was introduced after the filing of U.S. patent application Ser. No. 12/059,383.

Testing of Micro-Patches in Accordance with the Present Invention:

The results of the aforementioned micro-patch preparations, primarily with embodiments that utilize laser Doppler flowmetry for monitoring, are described below, in accordance with U.S. patent application Ser. No. 12/059,383, as well as U.S. Provisional Patent Application Ser. No. 60/920,823. All studies were performed with approval of the Human Investigations Committee of Yale University School of Medicine.

Study A. Nicotine Micro-patches and Single Channel Laser Doppler Flowmetry Probe at a Single Study Site Most of the work preliminary to the present invention was performed with customized modifications of a transparent nicotine patch. This was due to several reasons, including:

an FDA-approved nicotine transparent patch is available for clinical use; and systemic levels of nicotine are known to have significant cardiovascular effects, making customization important so as to avoid systemic effects; work with systemic levels of nicotine (administered by lozenge) [Mo C, Stout R G, Shelley K H, Tantawy H, Silverman D G:

Acute microcirculatory effects of nicotine in non-smoking volunteers. Anesthesiology 2004;101:A246] prompted assessing the effects of this drug at the level of the microvasculature in the absence of systemic drug levels and hence in the absence of systemic effects.

The preliminary investigations with nicotine micro-patches (0.83 mg/cm$^2$) entailed customizing a section of the micro-patch so that it adhered to an area of skin that was sufficient to deliver drug to the area under a laser Doppler flowmetry probe and that enabled attachment of the laser Doppler flowmetry probe to an upper surface of the micro-patch. This led to the following findings.

Figure 17:
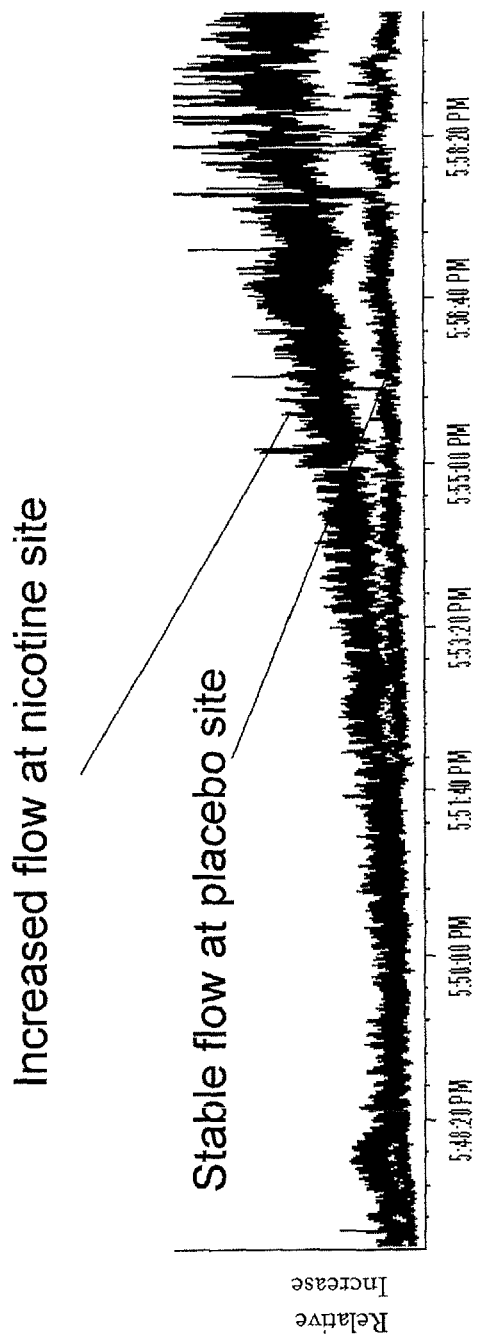
FIG. 17 shows continuous flow readings obtained with laser Doppler flowmetry probes placed at a site of a nicotine micro-patch (upper) and a placebo gel (lower) on the forehead in accordance with the present invention. x-axis=time in minutes; y-axis=voltage output (relative flow above baseline, values not shown). Between 5 and 15 minutes after application of the nicotine micro-patch, flow at the nicotine site increased progressively to approximately 300% of baseline, providing heretofore unknown information about the direct effect of nicotine on the microvasculature in this region (as opposed to information obtained after systemic administration).

As shown with reference to FIG. 17, transdermal application of nicotine at the cholinergically rich forehead (i.e., a region rich in acetylcholine receptors) causes a 2-5-fold increase in local blood flow within 30 min. A button-sized translucent nicotine micro-patch caused a 388.4% increase at the active site and a 2.9% increase at the placebo site when applied to the forehead of seven healthy subjects (two-tailed=0.012 for difference between nicotine and placebo sites). In the absence of parasympathetic pathways (e.g., because of location on distal extremities or because of damage by disease such as diabetes), the decline in micro-patch induced vasodilation is much greater with nicotine than nitroglycerin; for example there was no significant change when nicotine was applied to the finger, but there was a significant change, albeit less than at the forehead) with the nitroglycerin micro-patch. The difference likewise is seen in results generated by a laser Doppler scanner (discussed below). When drug delivery was limited to the micro-patch, the increase in flow was limited to skin at or adjacent to the site of micro-patch application; no response was evident at a remote site or in systemic indices (e.g., heart rate, blood pressure, flow at other sites).

Hence, this preliminary work identified the efficacy and safety (lack of remote effects) of micro-patch technology in accordance with the present invention and enabled attainment of information about the microcirculatory effects of nicotine that heretofore had not been appreciated [Mo C, Stout R G, Shelley K B, Tantawy H, Silverman D G: Acute microcirculatory effects of nicotine in non-smoking volunteers. Anesthesiology 2004;101:A246]. When the inventor queried ~20 colleagues as to what they anticipated the local microvasculature's response would be to a micro-patch with transdermal nicotine, they all believed that, as for systemic delivery of this agent, the micro-patch would cause vasoconstriction. However, it caused vasodilation because only parasympathetic (and not sympathetic) receptors are at the microvasculature. This shows the potential importance of isolating the local "acv" (that is, arteriolar-capillary-venous) microcirculatory responses with the micro-patch (as per Table 1). Nicotine's effect with the photoplethysmograph is elaborated upon in U.S. patent application Ser. No. 14/460, 082, entitled "Method and System Enabling Photoplethysmograph Measurement of Volume Status," which is incorporated by reference.

Figure 18:
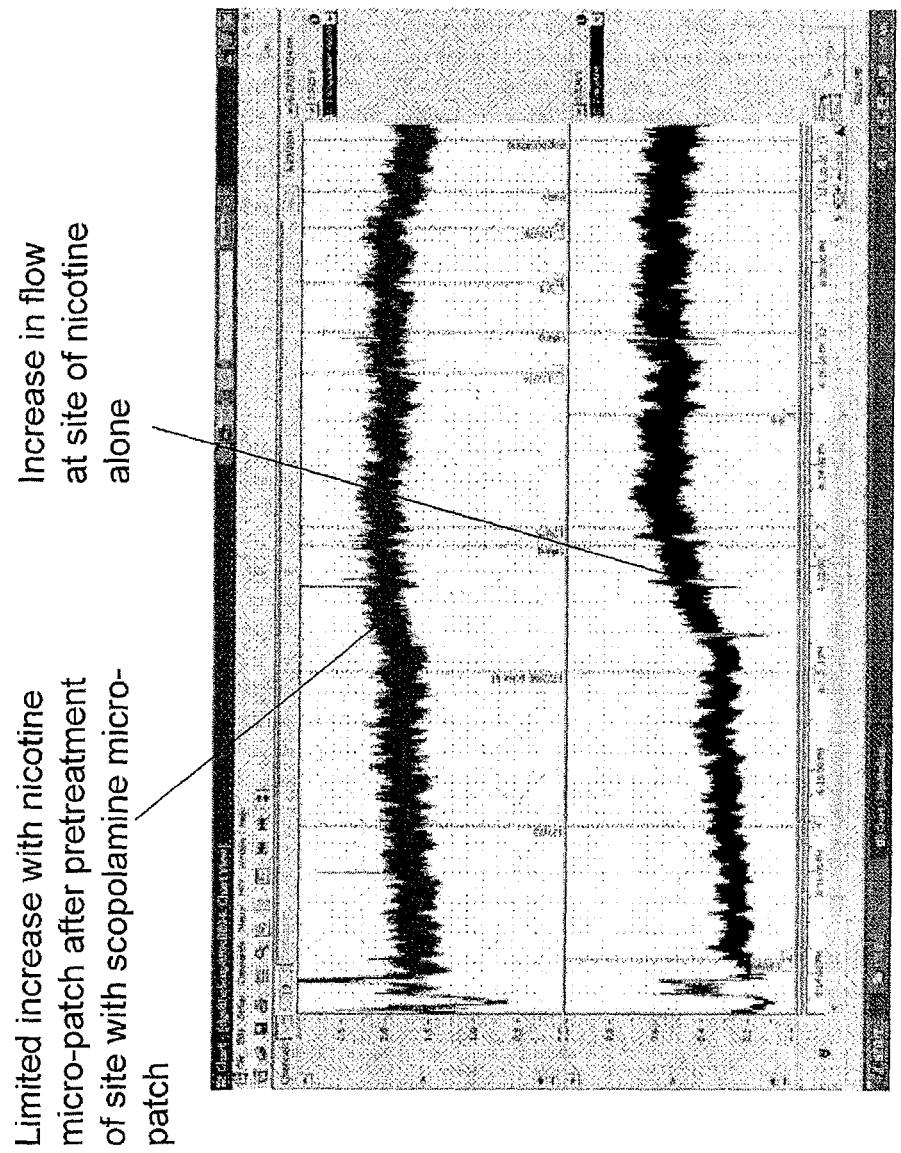
FIG. 18 shows tracings from two laser Doppler flowmetry probes on the forehead in accordance with the present invention, wherein the application of scopolamine before nicotine blunted the increase in perfusion seen with nicotine alone.

As shown in FIG. 18, embodiments of the inventive micro-patch technology provide the ability to monitor the effects of two agents applied concurrently. Here, the addition of scopolamine (top tracing) blunted the vasodilatory response induced by nicotine alone (lower tracing). Alternatively, the combination of a transdermal medication with a systemic medication enables what may be referred to as "dual platform" testing.

The initial assessments with the nicotine patch in accordance with the present invention also included assessments of light transmission properties and how they are impacted by micro-patches:

The laser Doppler signal was only slightly (and consistently) diminished by approximately 20% by placing a transparent covering (e.g., TEGADERM®) between the end of the monitoring laser Doppler flowmetry probe and the skin. This provided evidence that the laser Doppler flowmetry probe could sufficiently detect a signal through a clear micro-patch.

The laser Doppler signal was diminished immediately upon placing a clear NICODERM® micro-patch on the skin beneath the laser Doppler flowmetry probe, but the signal remained readily detectable. This attenuation was attributable to the impeded light path caused by the plastic backing (an impermeable plastic sheet that is thicker than a TEGADERM®) and the drug (nicotine)/inactive vehicle layer (—one manufacturer reported the contents to include acrylate adhesive, aluminized polyester, cellulose paper, and methacrylic acid copolymer). The consistency over time of the impedance of light transmission in the absence of a subsequent drug effect was tested by placing a clear NICODERM® micro-patch upside down (with the impermeable backing preventing delivery of drug). The equivalent decline in light transmission persisted for a 45-min testing period. Hence, it would not distort assessment of drug effect on perfusion.

Note—the clear NICODERM® patch that is commercially available was designed for cosmetic reasons, not to facilitate monitoring. It has writing on most of its surface, which impedes light transmission, and it is not of a desirable size for local testing. In accordance with the present invention, sections without writing were selectively punched out to create a translucent micro-patch for use in studies.

Study B: Clinical Application of Acetylcholine and Nitroglycerin Micro-patches

Testing of, and with, micro-patches in accordance with the present invention has been performed. In particular, micro-patches with two agents that more commonly are used to interrogate the microvasculature, acetylcholine and nitroglycerin, have been introduced.

This relates the responses to acetylcholine and nitroglycerin micro-patch preparations. Testing is reported in detail in Schonberger R B, Worden W S, Shahmohammadi K, Menn K, Silverman T J, Stout R G, Shelley K H, Silverman D G: Topical non-iontophoretic application of acetylcholine and nitroglycerin via a translucent patch: a new means for assessing microvascular reactivity. Yale J Biol Med 78:229-235, 2006, which is incorporated herein by reference.

Ten healthy volunteers and 10 patients with diabetes were recruited for laser Doppler flowmetry measurements of forehead perfusion at sites of transdermal application of acetylcholine, nitroglycerin, and placebo. This enabled confirmation that diabetes, a disorder compromised by systemic microvascular dysfunction, would be associated with a decreased vasodilatory response to a micro-patch applied to accessible microvasculature. The findings enabled generation of tentative cutoffs in a preliminary derivation data set which, after further refinement, will be tested in validation data sets. With the doses used, both nitroglycerin and acetylcholine induced significantly greater increases in flow in healthy volunteers than in patients with retinopathy as a consequence of diabetes. Typical tracings are shown in FIG.

Figure 20:
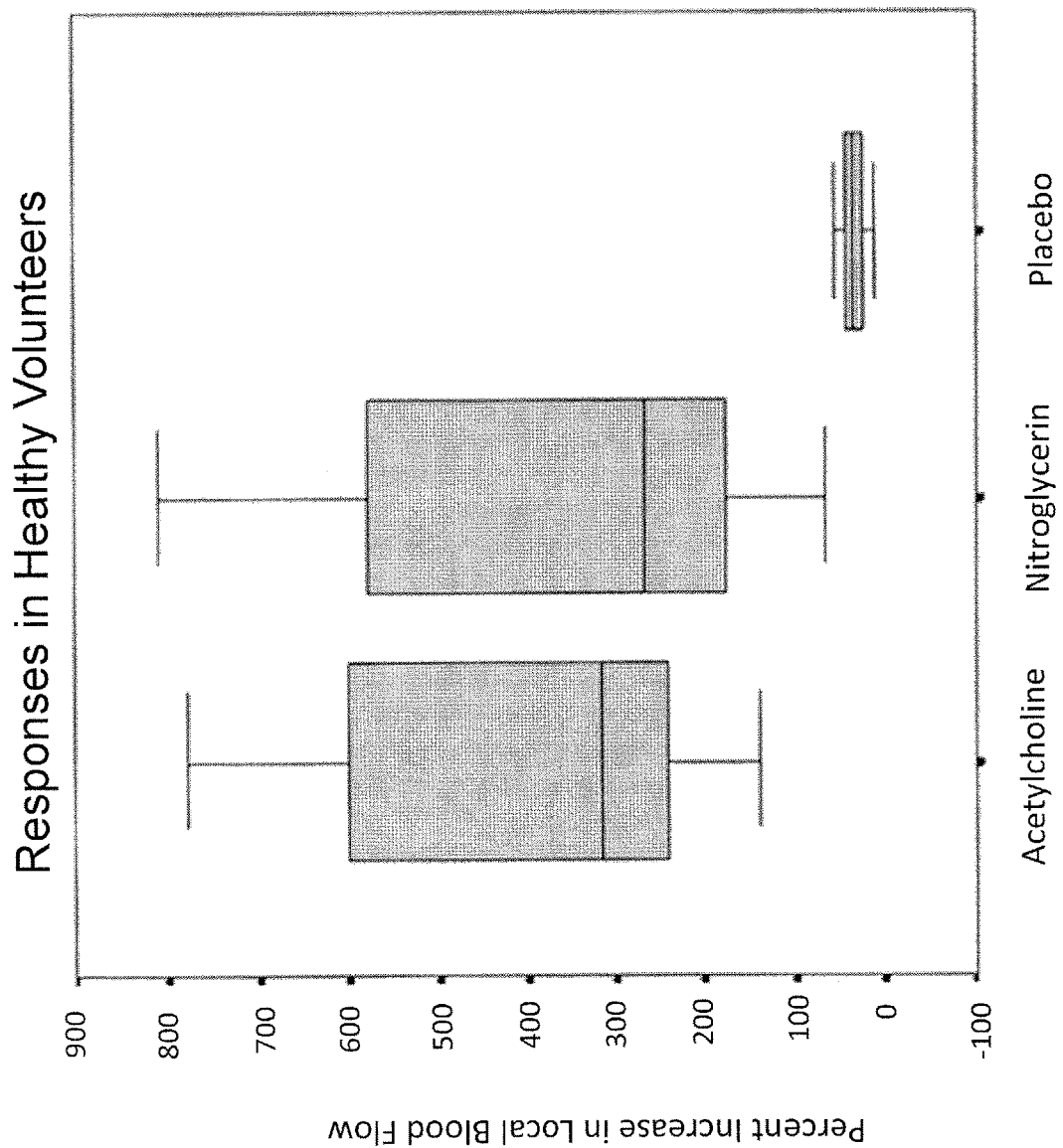
FIG. 20 shows boxplots summarizing the response to acetylcholine, nitroglycerin and placebo micro-patches in 10 healthy volunteers obtained in accordance with the present invention. Data are presented as mean percent increase in laser Doppler flowmetry voltage with 95% confidence intervals (CI).
Figure 21:
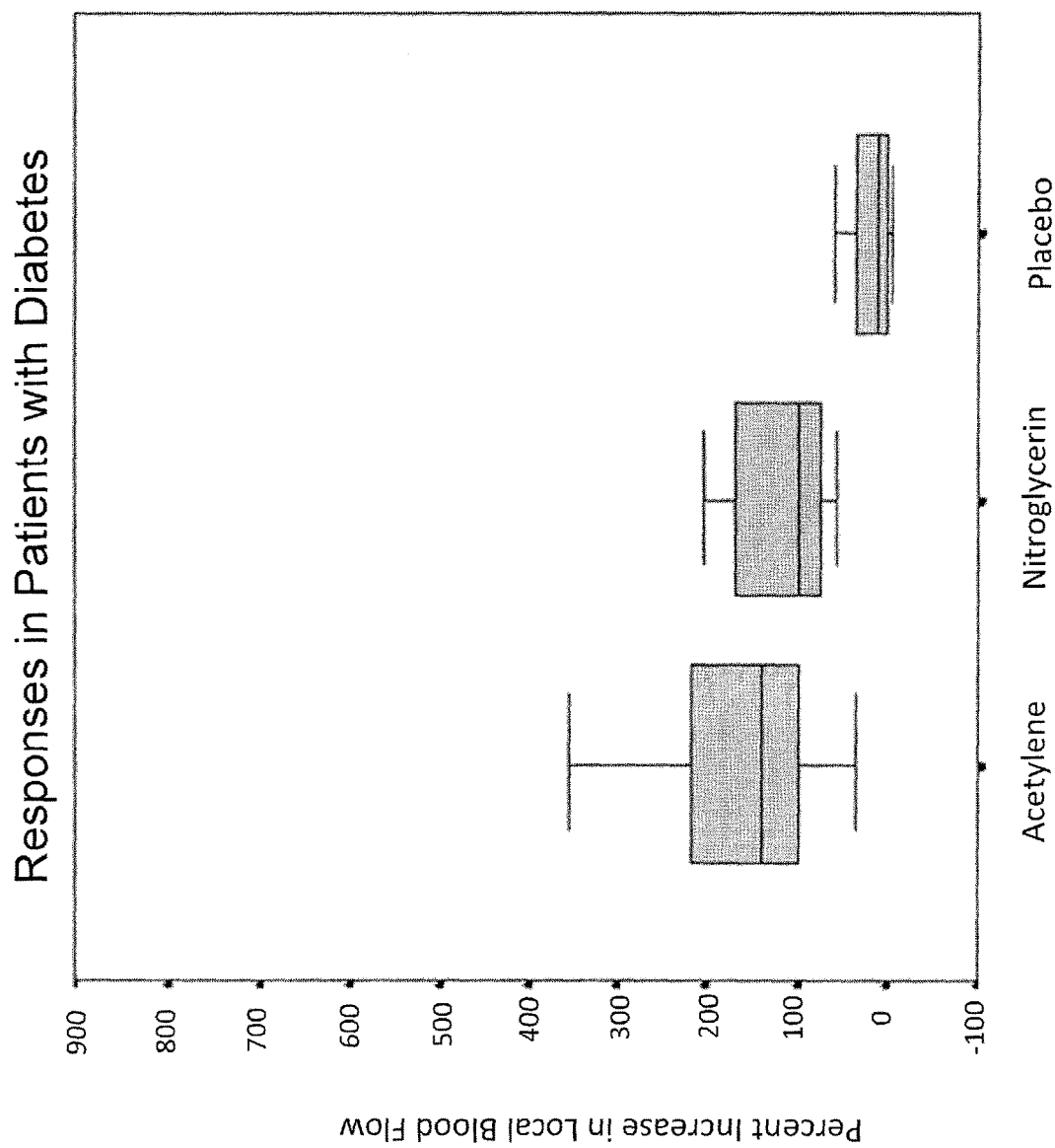
FIG. 21 shows boxplots summarizing reduced response of standard laser Doppler flowmetry to acetylcholine, nitroglycerin and placebo micro-patches in 10 patients with diabetes. Data are presented as mean percent increase in voltage with 95% confidence intervals (CI).

19; the different responses in healthy volunteers and patients are summarized in the boxplots of FIGS. 20 and 21, respectively.

It should be noted that, while the present disclosure does not provide an extensive array of cutoffs for specific disorders, the findings in diabetics indicate this is likely once customized micro-patches (desired local impact in accordance with objectives in Table 1) become available in FDA-approved designs. Then, local application of micro-patches will enable determination of local indices that pertain to the systemic circulation, more specifically compromise of the systemic circulation by systemic disorders.

Methods: For each session, subjects lay on a bed in a semi-recumbent position in a temperature-controlled room (24+1° C.). A three-lead electrocardiogram and a noninvasive brachial artery blood pressure cuff were applied. The three laser Doppler flowmetry probes with customized acetylcholine, nitroglycerin, and placebo micro-patches (as described above) attached were adhered onto the three double-stick discs on the forehead so as to enable undisturbed monitoring and drug delivery. Laser Doppler flowmetry monitoring was performed continuously at each site until a vasodilatory plateau was maintained for ≥3 minutes or for a maximum of 20 minutes. Data were collected at a rate of 1000 Hz using Chart for Windows (ADInstruments, Colorado Springs, Colo.).

The local microvascular effects of transdermal acetylcholine and nitroglycerin were first tested in 10 healthy volunteers (7 males, 3 females; mean age 36.1, range 19 to 56 years) without vascular disease or diabetes. The effects also were tested in 10 diabetic subjects (3 males, 7 females; mean age 56.5, range 40 to 73 years) recruited in the retina clinic of the Yale Eye Center, where they were being managed for diabetic-induced retinopathy (a disorder that is accompanied by microvascular injury). (This preliminary assessment did not match subjects for comorbidities and medications, nor impose dietary restrictions.)

An investigator blinded to the status of the subject and to the nature of the study site assessed the laser Doppler tracing at each study site. The pre-study trials had indicated that, within 10 seconds of laser Doppler flowmetry probe application, a steady baseline interval was consistently obtainable and that a progressive drug-induced rise in flow with both acetylcholine (top tracing in FIG. 19) and nitroglycerin (middle tracing in FIG. 19) was noted to begin no sooner than 30 seconds after probe application. This enabled a 20 second baseline period to be obtained, without the need to remove the laser Doppler flowmetry probe for subsequent drug application. This baseline period may be prolonged by means of delaying drug delivery such as agent encapsulation and/or introducing an inactive layer (see FIGS. 3-5) or by obtaining baseline readings before drug delivery (as per means for integrated delivery and monitoring shown in FIGS. 7 and 10, and for adaptive monitoring in FIGS. 12, 13, 14, and 16). Each laser Doppler flowmetry probe remained in place for up to 20 minutes. The drug-induced increase in flow in the present study was determined by comparing the mean during the lowest 10-second interval during the baseline period at the acetylcholine, nitroglycerin, and placebo (bottom tracing) sites with the mean during the maximum 10-second interval after a plateau was reached at the acetylcholine, nitroglycerin, and placebo sites. The effects of the single dose of acetylcholine was compared to the single dose of nitroglycerin in the healthy volunteers, with the differences analyzed using Wilcoxon Signed Rank Test (WSRT). Second, a preliminary assessment of the response in the healthy volunteers versus the 10 diabetic patients (who were older and had varied medical conditions and medications) were compared using the Mann-Whitney U Test (MWUT).

Results: Acetylcholine and nitroglycerin, but not placebo, induced a marked rise in laser Doppler flowmetry voltage (flux) within two minutes of drug application in each healthy volunteer. This was evident not only with respect to mean flow, but also with respect to the amplitude of the pulsation [AC (alternating current) component) coincident with each heart beat (see FIG. 19). Blood flow at the treatment sites remained elevated for the duration of the study session. Readings increased by 406% (245%-566%) and 36% (26%-46%), respectively, at the acetylcholine and placebo sites (p=0.005 by WSRT); and they increased by 365% (179%-550%) at the nitroglycerin site (p=0.005 by WSRT versus placebo; p=NS versus acetylcholine) (see FIG. 20). The absence of a systemic response was confirmed by the lack of significant dilation at the placebo site and by the lack of significant change in systemic blood pressure and heart rate. [Note: The slight (statistically insignificant) increase in flow at the placebo site is attributable to our team's investigative method for that study of comparing the highest 10 sec interval after drug application with the lowest 10 sec interval at baseline]

The vasodilatory responses to acetylcholine and nitroglycerin in diabetics were significantly greater than to placebo (see FIG. 21), but much less than in healthy volunteers. Mean percent increases in blood flow were 156% (91%-221%) and 116% (79%-153%), respectively, at the acetylcholine and nitroglycerin sites, vs. 21% (CI 4-37%) at the placebo site (p=0.005 by WSRT for placebo versus each active site). The responses of the diabetic patients to acetylcholine and nitroglycerin did not differ significantly from each other (p=NS by WSRT). The diabetics' responses at each active site were significantly impaired relative to healthy subjects (p<0.001 and p=0.009, for acetylcholine and nitroglycerin respectively, by MWUT).

Figure 19:
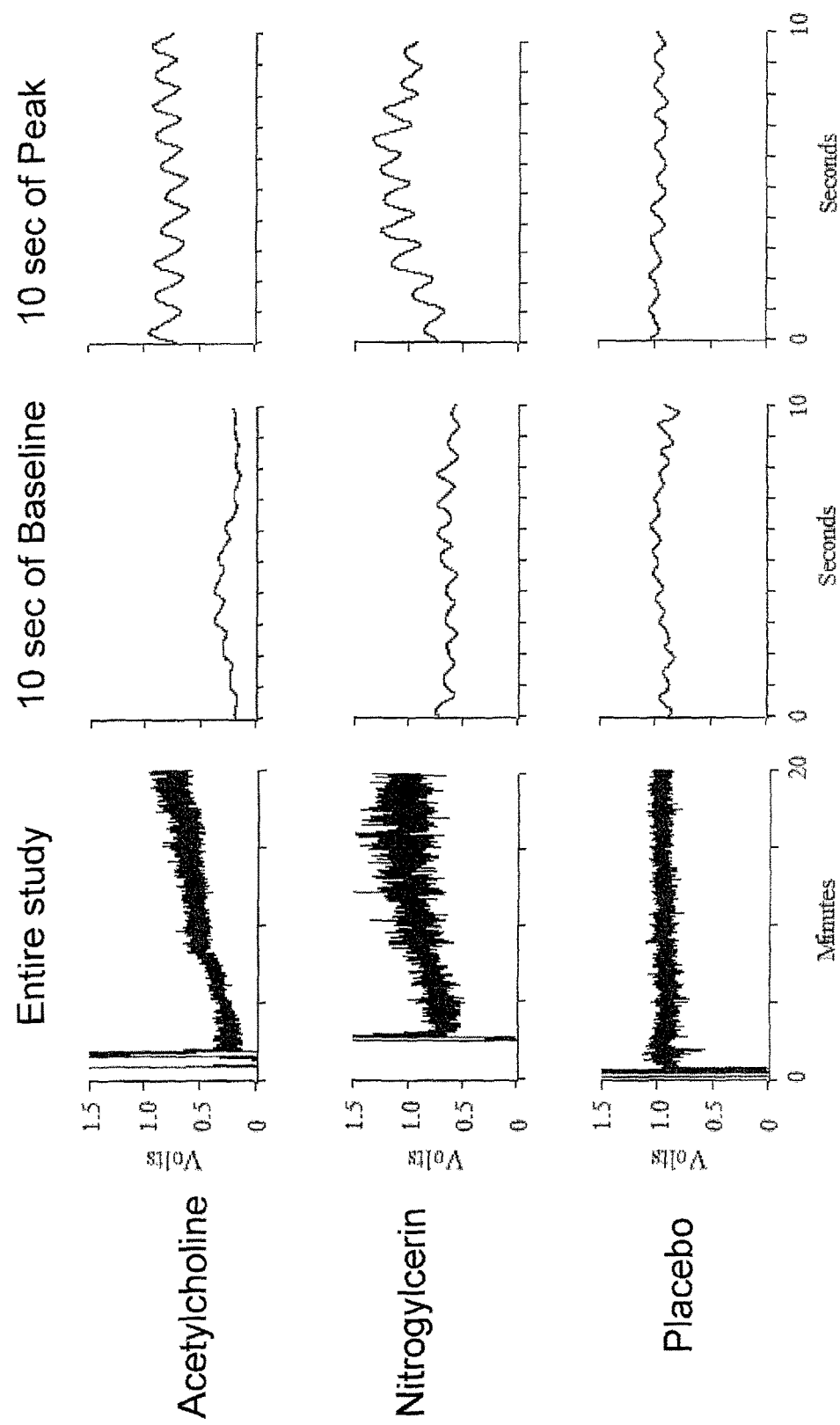
FIG. 19 is a series of graphs presenting representative data (laser Doppler values, in volts) from three laser Doppler flowmetry probes atop micro-patches on a healthy subject illustrating readings at the site of the inventive noniontophoretic micro-patch acetylcholine solution (top row), at the site of a nitroglycerin micro-patch (middle row), and at a placebo site (bottom row) in accordance with micro-patches introduced in the present invention. The entire 20 minute study period is shown in the left hand column; 10 seconds at baseline and 10 seconds during the plateau phase are shown in the middle and right hand columns, respectively. Prompt increases in blood flow at the sites of transdermal acetylcholine and transdermal nitroglycerin application are seen. This is manifested not only by an increase in mean flow but also in the amplitude of each pulsation at the cardiac frequency.

Comparison between FIGS. 17 and 19 shows that there is potential to regulate the rate of uptake based upon the nature of active agent and/or vehicle and/or patch construction: the onset of the different agents and their comparative effects on mean flow vs. the change in systolic amplitude (pulse height) and mean flow differed among the acetylcholine, nitroglycerin and nicotine micro-patches. The figures also illustrate that the stored data enables determination not only of mean flow, but also the impact of an agent on components of the pulse wave with each heartbeat, including peak (at systole), trough (at diastole), peak to trough, trough-to-peak upslope, and peak-to-trough downslope. Capture of the waveforms by sampling at a sufficient frequency (≥200 Hz in the present studies so as to also enable analysis of the electrocardiogram, but slower rates should be sufficient for laser Doppler flowmetry alone) to enable characterization of oscillatory activity and how it changed by the micro-patch. FIG. 19 shows that oscillatory activity appears greater at the acetylcholine site during baseline and at the nitroglycerin site during micro-patch application. Admittedly, this constitutes too little data to draw conclusions. Details for such assessments and their significance have been discussed in various papers [Silverman DG, Stout R G: Distinction between atropine-sensitive control of microvascular and cardiac oscillatory activity. Microvasc Res 63:196-208, 2002; Silverman D G, Stout R G, Lee F A, Ferneini E M: Detection and characterization of cholinergic oscillatory control in the forehead microvasculature in response to systemic alpha-agonist infusion in healthy volunteers. Microvasc Res 2001;61:144-7; U.S. Pat. No. 7,367,941 issued to David G. Silverman et al., entitled "Detection and Characterization of Cholinergic Oscillatory Control in Peripheral Microvasculature and Other Cardiovascular Signals", which is incorporated herein by reference]. Additionally, comparisons may vary, with respect to within-patch comparison to baseline as well as to a reference or placebo site, or as shown above for the comparison between acetylcholine and nitroglycerin, among agents.

Study C: Modifications of Monitoring Technique with the Laser Doppler Flowmetry Probe to Address Spatial Heterogeneity In that laser Doppler flowmetry constitutes a preferred mechanism of monitoring for the present invention, new mechanisms for overcoming the intrasubject variability caused by spatial heterogeneity among neighboring sites of a measure of perfusion such as laser Doppler flowmetry were introduced and evaluated. It showed that monitoring multiple data points in a tightly controlled measurement area can allow for a more accurate and reproducible determination of microvascular responsiveness in a given subject. The study consisted of two parts (approved my institution's Human Investigation Committee). The findings were presented by the inventor's team: Nissen A, Rose M, Schonberger R B, Silverman T J, Silverman D G: Consistency of laser Doppler assessments of vasoreactivity. American Society of Anesthesiologists 2A244:2006, which is incorporated herein by reference.

In part 1 (n=6 with "standard laser Doppler technique"), the effect of transdermal nitroglycerin on forehead blood flow was assessed through a portion of a translucent nitroglycerin patch with a standard 0.25-mm laser Doppler flowmetry probe (PF 5010, Perimed, Sweden) at a single site. Part 2 (n=4) was designed to minimize the impact of spatial heterogeneity by assessing the effect of transdermal nitroglycerin with the configuration shown in FIG. 16 at a fixed distance above the bridge of the nose. As detailed above, a seven-cable integrating laser Doppler flowmetry probe (probe 413, PeriMed, Sweden) 1 was mounted in a special support assembly 131 above the study site so that it could be moved in 1.25-mm increments in accordance with the present invention to obtain 16 measurements within a 1-cm$^2$ grid; the mean of the sixteen measurements was recorded. Each part consisted of two sessions at least 24 hours apart, wherein the nitroglycerin-induced increase in perfusion (from baseline) was recorded with the given probe after a vasodilatory plateau was reached within 10-20 minutes after chug application. Within each subject, the increase induced by nitroglycerin on the two days was compared; the Day 1 vs. Day 2 variation in response was expressed as % difference.

Figure 15:
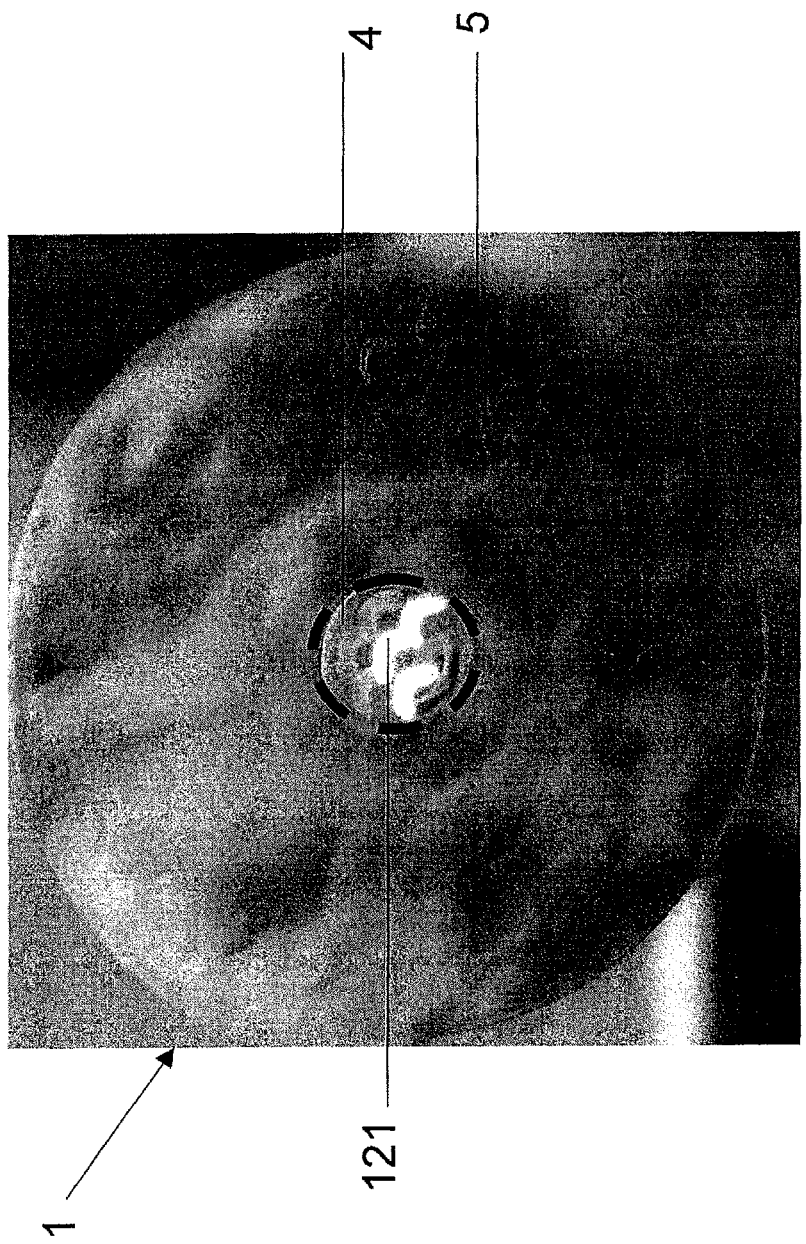
FIG. 15 is a bottom plan view showing a multi-channel probe. Three of the channels in the present embodiment are attached to a laser light source; the efferent signals from these three channels interface with separate laser Doppler sensors. The other four channels similarly may be configured for independent laser Doppler flowmetry or for other mechanism of assessing the microcirculation, potentially including photoplethysmography or tracer/substrate monitoring.

The findings illustrated the ability of both mechanisms to delineate changes induced by an inventive micro-patch. However, the techniques differed with respect to day-to-day variability. In Part 1 (standard probe), the mean day-to-day % difference averaged 100% (with a range of 20% to 300%) between the two study days. Conversely, in part 2 (integrating/multisite technique), the mean day-to-day % difference averaged only 20% (with a range of 10% to 30%) between the two study days. The relative day-to-day % difference with the integrating technique was significantly less than with the traditional probe (p=0.04; Mann-Whitney-U Test) To varying degrees, the increased consistency in the context of potential spatial heterogeneity reported above can be achieved in a variety of ways, including:

Use of the aforementioned integrating probe at a single location, with the option to mark the skin;
Use of a single channel probe at multiple neighboring sites;
Use of a multichannel probe (where the signal from each channel is assessed separately; FIG. 15) at one or more sites, with or without rotation at said site(s); and
Means for enabling persistent placement of monitors: e.g., micro-patches with microtubules 54 as shown in FIGS. 7 and 10; micro-patches with an area at one end 53 for anchoring to the skin as shown in FIGS. 6 and 7.

Study D: Impact of Fatty Meal (a Systemic Challenge) on Responses to Micro-Patches with Nitroglycerin and Acetylcholine This illustrates the use to acetylcholine and nitroglycerin micro-patches and the integrated probe technology to evaluate the effect of a potential systemic insult to the microvasculature. My team found that the ratio of endothelium-dependent to endothelium-independent vasodilation appears to be greater after a normal meal than after a fat-laden meal (which is an example of a dual platform. [Nissen A F, Cabo L, Silverman T J, Shelley K H, Silverman D G: Sensitivity of acetylcholine and nitroglycerin-induced vasodilation to endothelial impairment. Anesthesiology 2007;107:A291].

Methods: With Institutional Review Board approval, six healthy volunteers (3 male, 3 female) were recruited for a two-session study in which they randomly ate a fat-laden, 900 calorie meal or a fat-free meal of comparable calories. Two hours later, subjects underwent application of acetylcholine and nitroglycerin micro-patches. As described above, the former was prepared by mixing 100 mg of solid acetylcholine with 6 ml of sterile water. From this solution (concentration of 14.3 mg/ml) we used an aliquot of just under 0.14 ml (less than 10% of the standard 20 mg dose injected into the eye during cataract surgery). The latter consisted of a 1.4 cm×1.4 cm translucent square (cut from a full-sized nitroglycerin patch) to delivery 0.008 mg/hr of nitroglycerin to the study site. Before each patch application, seven sites of the forehead were monitored with a commercially available integrating laser Doppler flowmetry probe that averages the output from several closely packed light-transmitting channels (to partially overcome spatial heterogeneity). At 10 minutes after patch application, readings were repeated. Changes were analyzed using paired t-test.

Results: Although the response to acetylcholine was still present after the fat-laden meal, the relative increase induced by acetylcholine compared to that induced by nitroglycerin was significantly less than after the nonfat meal. The nitroglycerin/acetylcholine ratio was 1.31 and 0.94, respectively after the fat and nonfat meals (p=0.036). This application of the inventive micro-patches and customized means of inventive monitoring through the micro-patch indicated that, in response to a challenge which compromises endothelial function, the relative vasodilatory effect of acetylcholine was reduced compared to that of nitroglycerin. This is but one example of the potential applications of the inventive technology to address clinically relevant issues affecting the systemic microvasculature.

Integrated Display:

As noted above, a major advantage of the micro-patch is its induction of changes in the microvasculature at the study site without remote or systemic impact. This can be confirmed by monitoring at remote sites or by monitoring systemic indices such as a heart rate or blood pressure. This may be accomplished with a coordinated data acquisition system such as that shown in FIG. 26. This shows real-time input from four laser Doppler flowmetry probes (top four rows) and a continuous electrocardiogram tracing (bottom row). In addition to confirming the intended lack of remote or systemic responses, such a system can be used to identify such responses when they are being sought (as would be the case if one were performing dose-response studies and/or wishing to confirm that a given preparation is being absorbed even if it did not induce changes at the study site). This also can provide integrated display of the responses from different monitors. The acquired data are transferable to spread sheets for analysis of individual channels and comparative analyses among channels.

Alternative Micro-patch Embodiments:

It is contemplated embodiments of the drug-containing micro-patch could be an individualized combination of drug and adhesive (as described above for acetylcholine), a punchout/cutout from a larger patch (as described for nicotine and nitroglycerin), mass-produced button-sized units, or a peel-away unit from a larger strip, or different agents aligned at a distance to avoid overlapping impact on a strip. Alternatively, especially when monitoring does not touch the study site, the inventive "micro-patch" could take the form of precise aliquots of a "micro-applicant" that may consist of a thin layer of the preparation in accordance with the inventive concentrations and delivery described above, in a translucent vehicle without a backing. Not only would the unique micro-patching dosing and concentration and nonintrusive delivery introduced herein apply in such settings, but also the mechanisms for assessing the effects on the local microvasculature (e.g., availability of placebo, applicability to multiple sites, monitoring techniques, assessment of data). Nonetheless, preparation of a micro-patch with backing increases consistency of dosing and rate of delivery, is more amenable to applying layers (such as the inactive layer 32 and agent layer 34 in FIG. 3) and decreases the risk of contamination of other sites or the individual applying the drug.

As an alternative to the small micro-patch, a full-sized patch could have all but the monitoring site(s) covered with a custom-fitted impermeable shield. The number of sites and the size of each site would be determined by how much of the shield is removed. However, this involves the application of the patch to a larger area, with the potential for accidental overdose. Alternatively, large patches could be prepared with predetermined active "micro-patch" regions.

If one felt it necessary to eliminate the potential impact of the ointment or gel on the ability of the laser Doppler to detect a signal, the invention can be modified to include a very small drug-free zone underneath the planned site of probe placement. One means to do this is as follows: when the micro-patch is being coated with drug, a small piece of tape would be placed over the desired drug-free zone so that it did not acquire any drug. The tape could then be removed before applying the micro-patch to the skin; this would be the site at which the laser Doppler flowmetry probe (or alternative monitoring technique) would be applied to view the skin Preliminary trials indicate that the spread of drug in the adjacent tissues is sufficient to achieve an effect at an immediately adjacent site which is circumscribed by the micro-patch and/or vehicle. Specifically, data from the study shown in FIG. 18 indicate that the local effects of nicotine with this configuration (i.e., nicotine-induced increase in blood flow slightly beyond the bounds of the nicotine micro-patch) and of scopolamine (i.e., this caused inhibition of the effects of nicotine applied through a hole in a scopolamine micro-patch) showed that effective delivery could be achieved from adjacent areas to the small drug-free region of the micro-patch. If a hole (or opening) 82 such as that in FIG. 10 is used, it should be as narrow as possible while still ensuring support of the monitoring probe and/or allowing for administration of additional agent. Whereas a 10 mm diameter opening was effective for the combined assessment of nicotine and scopolamine (FIG. 18) settings, the precise dimensions would depend on the diffusibility of the specific agent(s).

Since the inventor's 2007-2008 filings of U.S. patent application Ser. No. 12/059,383 and U.S. Provisional Patent Application Ser. No. 60/920,823 of the original embodiments in accordance with the objectives of Table 1, the applicability of micro-patch testing of the microvasculature also has been tested with other micro-patches, including one created from a full-sized rivastigmine (Exelon®) patch.

Alternative Embodiments for Monitoring and Additional Micro-patch Studies:

Monitoring the responses of the local microvasculature may entail a wide range of techniques, including laser Doppler flowmetry via a monitoring probe, laser Doppler scanning, laser speckle imaging (discussed below), surface reflectance photoplethysmography, and measuring tracer substrate delivery and removal.

Initially, the micro-patch embodiments were tested primarily with laser Doppler flowmetry probes and a laser Doppler scanner Initial studies with a laser Doppler flowmetry probe and the inventive micro-patch were performed with a standard 1 mm diameter probe (described above). Traditionally, measurements have been made with a single laser Doppler flowmetry probe at a single site. The temporal variability that occurs with each heart beat (high at systole, low at diastole) and over the course of periodic oscillations (typically in the range of 1 every 5-20 seconds) can be overcome by monitoring at a single site for a sufficient period of time. The nature of the oscillatory activity also may provide valuable information as noted in the inventor's U.S. Pat. No. 7,367,941, entitled "Detection and characterization of cholinergic oscillatory control in peripheral microvasculature". The '941 patent, which does not address micro-patch technology, is incorporated herein by reference to the extent it is relevant to the present disclosure.

Consistent with other investigators who used laser Doppler flowmetry in varied settings, the inventor and his colleagues encountered intra-subject variability as a consequence of spatial variability at the microvascular level. As noted above, in 1992, the inventor co-authored a study that delineated the spatial heterogeneity of the microvasculature, wherein 1×1 mm monitoring sites with a 10×10 mm area had areas ranging from virtually no capillaries to a rich network containing many capillaries as well as an arteriole that was oriented horizontally (and thereby generate a maximal reading). [Braverman I M, Schechner J S, Silverman D G, Keh-Yen A: Topographic mapping of the cutaneous microcirculation using two outputs of laser-Doppler flowmetry: flux and the concentration of moving blood cells. Microvascular Research 44(1):33-48, 1992 July]. The variability is such that taking the laser Doppler flowmetty probe off and replacing it may result in a significant change in laser Doppler values and, as the inventor has shown in trials with the micro-patch, in the measured response to a vasoactive drug. That is, one can get greatly different blood flow measurements depending on where the laser Doppler flowmetry probe is attached even within a fairly confined area on, for example, the forehead. This makes it harder to accurately analyze the effect of interventions done on different days aimed at altering blood flow, as one does not know whether the change in flow seen is secondary to the intervention or just a consequence of looking at a different vascular bed compared to the readings from the control day. Mechanisms to address this in the context of a micro-patch with the use of a multichannel integrating probe, a multichannel nonintegrating probe and/or a special assembly are discussed above and illustrated in FIGS. 15-17. Additionally, there is the option to use the inventive micro-patches with embedded microtubules 54 (FIGS. 7 and 10) and/or anchoring at the base (FIGS. 6 and 7) so as to ensure consistent alignment after temporary elevation (so as to apply drug at one or more micro-patch sites.

Another alternative is provided by the laser Doppler scanning imager. In 1994, the inventor co-authored a study confirming the spatial heterogeneity with a laser Doppler scanner. [Wardell K, Braverman I M, Silverman D G, Nilsson G E: Spatial heterogeneity in normal skin perfusion recorded with laser Doppler imaging and flowmetry. Microvascular Research 48(1):26-38, 1994 July]. This demonstrated the value of site-by-site mapping as a means of identifying and potentially overcoming spatial heterogeneity. This is accomplished by rapidly scanning an area by a shifting light that is sequentially directed to successive study sites by a mirror. Although this eliminates some of the problems associated with probe movement, it does not eliminate the problems associated with temporal variability when measurements are successively obtained at neighboring sites. This is because the laser Doppler scanner typically monitors a given site for fractions of a second. Hence, it is less likely to identify pulsations and oscillations in the microcirculation and potentially more likely to be distorted by them. Compromises include rapidly scanning all sites at repeat intervals for a long enough period to overcome the effects of pulsations and oscillations. However, a relatively long interval is required to ensure this. Thus, the laser Doppler scanner mitigates spatial variability at the expense of temporal variability (e.g., beat-to-pulsations with each heart beat as well as oscillations in activity as a component of autonomic regulation of blood vessels).

The micro-patch technology introduced herein is technologically well-suited to monitoring with a laser Doppler scanner; as for the elevated probe assembly (FIG. 16), it does not entail application of the monitoring device to the study site surface and thus is amenable to the alternative micro-applicants discussed above. As illustrated in FIGS. 22-25, the laser Doppler scanner can delineate gradations in blood flow in response to a micro-patch.

Figure 22:
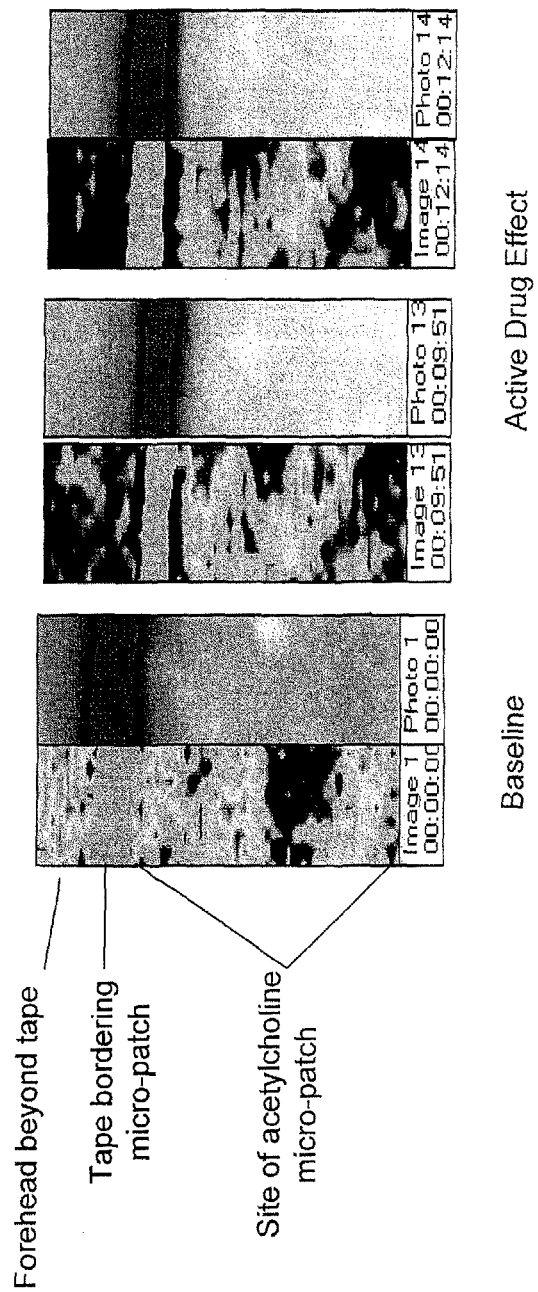
FIG. 22 shows images obtained with laser Doppler scanner depicting relative flow on left and actual picture of site on right before (image 1) and during application of acetylcholine micro-patch to middle of the scanned area of the forehead. Note—the nature of this commercial device is such that gray scale is specific for each image; hence black in one image actually could represent greater flow than gray in another image. Images at 09:51 and 12:14 minutes show lighter areas in the region of drug application (compared to the untreated upper region), indicating increased blood flow as a result of the acetylcholine.
Figure 23:
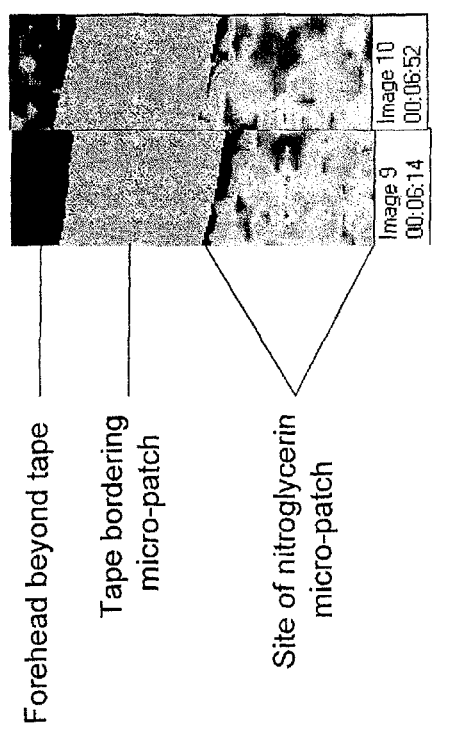
FIG. 23 shows images with laser Doppler scanner in accordance with the present invention 6:14 and 6:52 minutes after application of nitroglycerin micro-patch to the forehead. Increased flow is evident in region of the micro-patch (below the tape).
Figure 24:
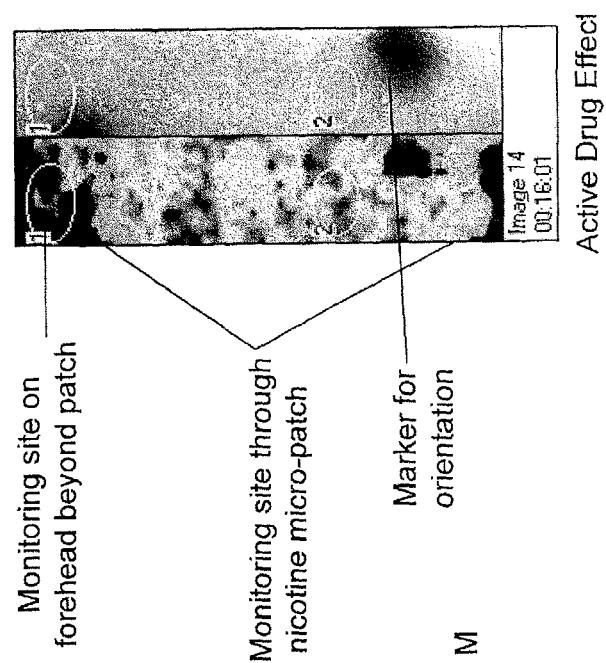
FIG. 24 shows an image and picture obtained with laser Doppler scanner in accordance with the present invention 16:01 minutes after application of nicotine micro-patch in the mid-60% of the scanned area of the forehead. Shades of gray illustrate greatest flow in the area of nicotine micro-patch application.

The increase at the forehead site of the acetylcholine, nitroglycerin and nicotine micro-patch application in accordance with the present invention are shown with the laser Doppler scanner in FIGS. 22, 23 and 24, respectively. Each figure shows relative flow on left and actual picture of site on right. In each case, images obtained several minutes after micro-patch application show an increase in relative blood flow (color/gray scales) at the site of drug application (below the tape that identifies the border of the micro-patch. (As stated above, it is important to note that the nature of this commercial device is such that gray scale is specific for each image; hence black in one image actually could represent greater flow than gray in another image).

An important feature of the present invention is the ability to distinguish responses among different agents at different sites. The laser Doppler images of two fingers in FIG. 25 illustrate this advantage but it should not be construed that such an advantage would not be obtainable with another mechanism of monitoring such as laser Doppler flowmetry, photoplethysmography or tracer/substrate sampling probes at each site. Whereas both a nitroglycerin micro-patch (FIG. 23) and a nicotine micro-patch (FIG. 24) caused vasodilation in the forehead, FIG. 25 shows that only the nitroglycerin micro-patch induced vasodilation in the finger. This illustrates the applicability of the present invention to compare different agents at a given region as well as to compare a given agent at different regions—specifically, the data are consistent with the belief that nicotine induces vasodilation at the preganglionic-postganglionic junction of parasympathetic (cholinergic) pathways; these pathways are rich in the forehead and sparse in the finger. Nitroglycerin induces vasodilation independent of the parasympathetic pathways. This disparity is consistent with the reporting by the inventor's team of disparate responses of the finger and forehead after systemic administration of nicotine [Mo C, Stout R G, Shelley K H, Tantawy H, Silverman D G: Acute microcirculatory effects of nicotine in non-smoking volunteers. Anesthesiology 2004;101:A246] and phenylephrine [Silverman D G, Stout R G: Distinction between atropine-sensitive control of microvascular and cardiac oscillatory activity. Microvasc Res 63:196-208, 2002]. These studies also provided evidence of sympathetic predominance in the finger and of a relatively greater degree of cholinergic (parasympathetic) activity in the forehead. Such discrimination by a noninvasive micro-patch technique should be extremely helpful in clinical settings.

The aforementioned ability to delineate these distinctions between drugs and locations constitutes a major advantage of the present invention with respect to: comparing agents; comparing sites; identifying which steps in microvascular vasoconstrictive and vasodilatory processes are activated; and assessing the impact of disease, therapies and other interventions.

Limitations of the laser Doppler scanner include higher cost and a more elaborate setup that enables mounting of the laser Doppler scanner above the area of interest. Further, and since available scanners scan each site sequentially, the use of an onsite probe (as opposed to a moving scanner) is preferable if one seeks to delineate the time course of changes or to look at oscillatory changes in blood flow at a given site. However, this also may be accomplished by fixing the laser Doppler scanner at a given test site. Limitations also include other aspects of temporal variability discussed above.

Potential options for scanner development to enable simultaneous monitoring of multiple sites, as would be desirable in the context of the inventive micro-patch, include:

1. single source with a lens (diffractor) that enables delivery and capture of signal from multiple sites at a given session;
2. sends and receives signals via multiple mirrors;
3. multiple light sources that reflect at different sites on a single mirror;
4. multiple beams and multiple mirrors; and
5. incorporating other sites by changing orientation of light source and/or detectors, changing angle of mirror, or moving the mirror(s).

These necessitate costly and cumbersome devices.

The limitations imposed by spatial and temporal resolution may be overcome by laser speckle imaging. Here, a single laser light that generates a "speckle" as a result of reflection from a heterogeneous surface such as skin. This speckle is blurred in proportion to a dynamic process such as blood flow. The sequential blurring is determined by simultaneous sampling by a multitude of pixels in a standard charged coupled device (CCD) camera array. There is concern, however, that this may not provide the sensitivity to changes in flow afforded by laser Doppler flowmetry, especially if such changes are subtle or compromised by a disease state. Additionally, the speckle pattern may be affected by the consistency of a micro-patch, which might change over the course of time on the skin.

If the laser speckle imager alone cannot effectively document oscillatory activity, then coupling it with a laser Doppler device may overcome this problem. One could set this up so that when one went into the laser Doppler mode, the following would occur:

- The efferent link from only a selected number of pixels would be recorded on a CCD; the other pixels on the CCD would virtually be turned off. This would provide a limited output from either a single pixel or a cluster of pixels that would represent a given vascular territory.
- The output from the selected pixels would be analyzed by the laser Doppler component to determine frequency shift (degree of shift and amount of shift, i.e., the CMBC and flux components).
- This could simply require an output cable. The operator could select the pixel or cluster of pixels that should be used to generate signal for laser Doppler analysis; or this could be automated to select the highest pixel (if that alone would give sufficient amount of light) or the highest cluster of pixels, wherein each highest cluster of pixels wherein each pixel is within a fixed percentage, (e.g., 10% of the highest value).

In addition to other potential embodiments based upon the teaching herein, the embodiments shown in FIGS. 1, 2, 6, 7, and 26 are suitable for concurrent monitoring of multiple parameters at the same site (i.e., beneath the same micro-patch). For example, laser Doppler flowmetry can be accomplished in the manner described above; and PPG signal can be obtained by transmittance or reflectance PPG as applied in studies described above. This not only will enable one to identify how a given micro-patch specifically affects a component of the arteriolar-capillary-venule network but also can be applied to assess differences in the absence of drug.

The present invention also introduces new mechanisms of assessing and analyzing multiple parameters recorded in concert—e.g. flow (as measured by laser Doppler flowmetry) and volume (as measured by photoplethysmography (PPG)). These inventive methods were preceded by a study (presented at the 2012 annual meeting of the American Society of Anesthesiologists by the inventor's research team) wherein we tested my proposal to compare pulse transit times (PTT) between the onset of pulsatile wave (AC component) of the PPG (largely dependent upon delivery of stroke volume via the artery proximal to the acv network) and of the laser Doppler (with the incremental PIT largely dependent upon transfer of stroke volume from the artery under the PPG to the acv network). This identified an inter-device (arterial to acv) delay of 0.120 sec at the ear and 0.108 sec at the finger. However, this comparison of PTTs was limited by: a) lack of a device capable of recording these parameters at a common site (i.e., over the same micro-patch, a introduced above); and b) the differing nature of the monitor signals such that criteria for onset differed for measure of flow (laser Doppler) and measure of volume (PPG). This leads to present disclosure of a means to overcome the potential confusion: I herein introduce the application of spectral domain analysis [fast Fourier transformation (FFT), alluded to above, and variations thereof such as joint time frequency)] to characterize PTT values. This enables comparative assessment of: FFT of $PTT_{PPG}$ (primarily influenced by arrival of the stroke volume at underlying artery), FFT of $PTT_{laserDoppler}$ (arrival of stroke volume at microvasculature), and FFT of $PTT_{PPG\text{-}LaserDoppler}$. An example of this process is shown in FIG. 27. This displays the FFT of the PTTs of the PPG and laser Doppler on the forehead of a resting volunteer (nearby untreated sites) and the FFT of the PTT between the two monitors. The FFT displays show a predominance of oscillatory power between 0.11 and 0.17 Hz (in the intermediate frequency band), suggestive of parasympathetically mediated regulation of the vasculature between the vessels primarily responsible for the PPG and laser Doppler measurements.

This not only facilitates inter-device comparison and calculation of inter-device differences through common units (e.g., volts/Hz for amplitude density of the FFT of PTT oscillatory patterns), but has the added advantage of obviating the confusion as to the onset time of each device (as onset criteria would not significantly distort FFT comparisons). As of now, the clinical value of the related inventive embodiments (for monitoring in the presence of a micro-patch) remains speculative due to lack of a device that provides simultaneous laser Doppler and PPG readings at the same site. However, the potential for such monitoring is evident in several embodiments, including those shown FIGS. 1, 2, 6, 7, 15 and 26. In addition, my above-noted finding that FFT showed marked oscillatory activity at nicotine (but not nitroglycerin) micro-patch sites attests to the information obtainable with FFT: the nicotine site showed a marked increase in the 0.03-0.12 Hz frequency range which is indicative of sympathetic activity, a "normal" homeostatic response to nicotine-induced release of acetylcholine (the mediator of parasympathetic effects). Once combined monitoring becomes available at a given site, and then concurrent FFT analysis of PTT of artery, acv and vein will enable one to delineate the sites of microvascular and neuro-microvascular activity. In addition to micro-patch induced changes in readings between sites of measurement (e.g. PTT), we can also measure changes at sites of measurement (e.g., mean, heights). Again, confounders such as different units and differing criteria for onset may be avoided with FFT. For this, the ability to convert continuous (e.g., raw signal) and noncontinuous (e.g., heights) signals into pseudocontinuous signals for uniform FFT analysis is incorporated into the present invention (as shown in U.S. Pat. No. 7,367,941 issued to David G. Silverman et al., entitled "Detection and Characterization of Cholinergic Oscillatory Control in Peripheral Microvasculature and Other Cardiovascular Signals", which is incorporated herein by reference).

Unique Applications of Inventive Designs and Methods:

It is contemplated the present invention will be utilized in multiple settings, including:
- Dermatological conditions with altered perfusion
- Atherosclerosis, coronary artery disease, and peripheral vascular disease
- Diabetes with the suspected or documented autonomic neuropathy, vasculopathy and/or end-organ disease
- Hypertensive, prehypertensive, or potentially prehypertensive patients
- Patients with eclampsia of pregnancy
- Patients with migraine and/or menstrual headaches
- Pain states with an autonomic component
- Altered autonomic control in patients with congestive heart failure
- Assessments of altered microvascular autoregulation
- To document disease progression
- To test effectiveness of potential therapies
- To document effectiveness of a prescribed therapy
- To perform integrated "dual platform: assessments of systemic and locally applied medications (and thereby minimize systemic interactions; e.g., to evaluate the potentially harmful systemic interaction when sildenafil (Viagra) and nitroglycerin both are administered systemically. The present invention enables the administration of one of the drugs (e.g., nitroglycerin) in a micro-patch in a single site, without the risk of dangerous systemic interaction.

To document unanticipated/undesirable effects of a given therapy. For example, as noted above, testing of a transdermal micro-patch preparation of rofecoxib (Vioxx, Merck Inc) may have identified compromised perfusion at the level of the microvasculature.

Establish dose response curves for individual agents or combination of different agents.

Identify site(s) of impact along the arterial-arteriolar-capillary-venule-vein (AacvV) network.

In summary, the present disclosure describes the development and initial implementation of the designs and methods to interrogate the local microcirculation during/after noninvasive, non-iontophoretic transdermal delivery of vasoactive agents, without concern about significant systemic effects. As such, the claimed invention provides heretofore unattainable ability for undisturbed, unaltered, and unmodulated pharmacologic activation of the local microvasculature at a site accessible to locally effective trans-surface drug delivery. This enables previously unattainable assessment of an individual's microvasculature with a study agent of known pharmacologic properties at an accessible site so as to assess—because of its known similarity—the status not only of the given site but also of less accessible regions (e.g., of vital organs) of the systemic microvasculature; and thereby identify and assess a condition's impact on the microvasculature. By being specific for the local microvasculature, as opposed to the more widespread impacts of more widespread interventions, the inventive findings are not confounded by changes in systemic indices and/or different (e.g., larger vessels).

The potential value of the invention was indicated by prior evidence (derived from prior art invasive assessments that are not amenable to routine clinical use in accordance with the criteria of the instant invention). Prior to the instant invention, such monitoring revealed that conditions which impact the microvasculature of vital organs similarly impact the microvasculature in the periphery; e.g., the impacts of atherosclerosis and diabetes not only affect the vessels of the heart, brain and kidneys, but also of the cutaneous vasculature. However, until the instant invention, the application of this knowledge was limited, because clinicians and researchers lacked a noninvasive, nondisturbing means to isolate changes at the level of the microvasculature and thereby readily assess the status of the microvasculature and hence overall microvascular health and responsiveness.

Certainly those skilled in the art would appreciate that readily repeatable testing can show whether a given abnormality is progressing or has improved. It is anticipate that the ability to clearly assess endothelium-dependent and endothelium-independent dysfunction will enable investigators and clinicians to perform correlative assessments with different disease states in clinical trials. This may lead to cutoffs for defining different disease states and for prompting therapeutic interventions. The potential for this is shown in U.S. patent application Ser. No. 12/059,383 by establishing a preliminary cutoff for diabetics with respect to their responses to acetylcholine and nitroglycerin. One could establish an index such that the degree of responsiveness is indicative of presence and severity of a disorder. Although it is premature to provide a well-defined index at this time, the data in FIGS. 20 and 21 suggest that an increase in response to transdermal acetylcholine in the forehead of <33% of that in control subject was consistent with advanced diabetic vascular dysfunction.

A major benefit of micro-patch technology is for receptor targeting. Even if they target a specific receptor, systemically administered drugs induce multiple effects beyond those at the site. This is especially evident for a drug like nicotine which activates preganglionic to postganglionic fibers throughout the sympathetic and parasympathetic nervous system. It therefore is difficult to discriminate between local and systemic effects. In contrast, only the parasympathetic nervous system has preganglionic to postganglionic synapses at the level of the microvasculature. Hence, micro-patch delivery of nicotine can selectively target those structures and enable assessment of their function in health and disease. However, it also is important that, in addition to being local, the micro-patch must be nondisturbing. Local delivery by a means such as iontophoresis may obscure the targeted response of the given agent because of the electric current and/or vehicle.

This is only the tip of the iceberg as to the potential applications of this technique. For example, it enables benign testing of potential microvascular dysfunction in cognitive disorders such as Alzheimer's disease (using micro-patches to help assess the conditions as well as potential means to treat them). Without the claimed technique most clinical trials to assess the evolving status of the microvasculature would not be possible or practical. Putting it briefly, the invention allows the clinician investigator to test locally and think (and potentially treat) systemically.

Furthermore, once an FDA-approved micro-patch is available it could be readily usable for clinical studies without concern about inconsistent dosing or related problems as a consequence of mixing one's own preparations (e.g., acetylcholine) or cutting patches (not intended for such a purpose and not FDA-approved for clinical use for said purpose). One could tailor any or all features (e.g., dose, rate of delivery). This would facilitate serial monitoring of severity. Based upon those clinical trials, one would then be able to not only think systemically but also act (diagnose and treat) systemically.

It is further contemplated confirmation of drug delivery in the absence of systemic, remote, or even local changes may be accomplished by a number of techniques known to those skilled in the art. These include: assaying agent levels remaining in micro-patch, tissue surface and within tissue; radioactive or fluorescent labeling to determine amount remaining and/or amount in the tissue.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A system for assessing local microvasculature and local microcirculatory vasoreactivity of a patient or research subject by selective noninvasive and nondisturbing monitoring of local microvasculature and local microcirculatory vasoreactivity at an accessible site to noninvasive and nondisturbing trans-surface delivery of a study agent with a known microvascular effect in normal subjects, comprising:

a micro-patch noninvasively delivering a study agent to a study surface for trans-surface delivery to the microvasculature of the subject in non-iontophoretic manner, the micro-patch having a diameter of approximately 0.25 cm to approximately 2.5 cm and delivering less than or equal to 10% of the study agent used clinically to induce a systemic effect to exclusively affect local microvascular vasoreactivity without unwanted system effects, wherein the microvasculature consists of arteriolar-capillary-venule components of an arterial to venous network including neural structures which selectively innervate microvascular components, the micro-patch further includes an opening and embedded microtubules for infusion via the opening or areas beneath the micro-patch, the opening being shaped and dimensioned for access by a monitoring probe secured to the micro-patch;

the monitoring probe measuring alterations in perfusion of the microvasculature of the subject relative to a baseline reading in only an area of the study surface beneath the micro-patch without alteration of measurements by spread to neighboring sites or by systemic effects, the monitoring probe being selected from the group consisting of a laser Doppler flowmetry, a laser Doppler scanner, a laser speckle and a photoplethysmograph; and;

wherein the system provides a mechanism for determining the patient or research subject's microvascular responsiveness by measuring changes in microvascular perfusion in an area of skin of the patient or research subject beneath the micro-patch.

2. The system according to claim 1, wherein the micro-patch includes a transparent backing and a protective cover member, and the study agent to be delivered is structured to delay delivery of the study agent.

3. The system according to claim 1, wherein the micro-patch includes mini-projections.

4. The system according to claim 1, wherein the micro-patch includes reverse projections that extend into the micro-patch to open up channels for delivery of the study agent.

5. The system according to claim 1, wherein the system provides a mechanism for assessing microcirculatory impact of a pharmaceutical agent.

6. The system according to claim 1, wherein the monitoring probe measures exogenous and endogenous substrates.

* * * * *